United States Patent [19]
Uneme et al.

[11] Patent Number: 5,633,375
[45] Date of Patent: *May 27, 1997

[54] GUANIDINE DERIVATIVES THEIR PRODUCTION AND INSECTICIDES

[75] Inventors: Hideki Uneme, Osaka; Koichi Iwanaga, Ikeda; Noriko Higuchi, Matsubara; Isao Minamida, Kawabe-gun; Tetsuo Okauchi, Hirakata, all of Japan

[73] Assignee: Takeda Chemical Industries, Ltd., Osaka, Japan

[*] Notice: The term of this patent shall not extend beyond the expiration date of Pat. No. 5,489,603.

[21] Appl. No.: 481,136

[22] Filed: Jun. 7, 1995

Related U.S. Application Data

[62] Division of Ser. No. 91,744, Jul. 15, 1993, Pat. No. 5,489,603, which is a continuation of Ser. No. 707,916, May 30, 1991, abandoned, which is a division of Ser. No. 456,863, Dec. 27, 1989, Pat. No. 5,034,404.

[30] Foreign Application Priority Data

| Dec. 27, 1988 | [JP] | Japan | 63-332192 |
| Jan. 31, 1989 | [JP] | Japan | 1-023589 |
| Jul. 19, 1989 | [JP] | Japan | 1-187789 |

[51] Int. Cl.$^6$ .......................... A01N 43/40; C07D 213/24
[52] U.S. Cl. .......................... 544/336; 546/332; 548/146; 548/200
[58] Field of Search .................... 546/329, 332; 544/53, 336; 548/146, 200

[56] References Cited

U.S. PATENT DOCUMENTS

| 3,897,444 | 7/1975 | Durant et al. | 548/202 |
| 4,108,859 | 8/1978 | Tong | 546/289 |
| 4,220,654 | 9/1980 | Bolhofer et al. | 514/397 |
| 4,590,195 | 5/1986 | Alker et al. | 514/252 |
| 4,604,393 | 8/1986 | Cornu et al. | 514/229 |
| 4,640,926 | 2/1987 | Sach | 514/333 |
| 4,742,060 | 5/1988 | Shiokawa et al. | 514/252 |
| 4,948,798 | 8/1990 | Gsell | 514/318 |
| 5,034,404 | 7/1991 | Uneme et al. | 514/365 |
| 5,063,236 | 11/1991 | Gsell | 514/275 |
| 5,384,324 | 1/1995 | Shiokawa et al. | 514/365 |
| 5,489,603 | 2/1996 | Uneme et al. | 514/365 |

FOREIGN PATENT DOCUMENTS

| 0113070 | 7/1984 | European Pat. Off. |
| 0254859 | 2/1988 | European Pat. Off. |
| 0268915 | 6/1988 | European Pat. Off. |
| 0306696 | 3/1989 | European Pat. Off. |
| 0364844 | 10/1989 | European Pat. Off. |
| 0375907 | 7/1990 | European Pat. Off. |
| 53-108970 | 9/1978 | Japan . |
| 59-118767 | 7/1984 | Japan . |
| 64-70467 | 3/1989 | Japan . |
| 1-325327 | 12/1989 | Japan . |
| 2-209868 | 8/1990 | Japan . |

OTHER PUBLICATIONS

Moriguchi,I., Komatsu, K., Matsushita, Y. J. Med. Chem. 1980, 23, pp. 20–26. 1980.
Derwent Publications Ltd., J5 4079–271, Otsuka Pharm. KK, 1979.
Fye et al., "Chemisterilants for the House Fly", J. Agr. Food Chem., vol. 22, No. 3, 1974.
Nielsen et al., "Synthesis and Hypotensive Activity of N-Alkyl –N''–cyano–N'–pyridylguanidines, Journal of Medicinal Chemistry, vol. 21, No. 8, 1978.
Konig, Zeitschrift Für Naturforschung, W. 22, 194 E. 1973, Teil, B, pp. 814–819.
Canadian Journal of Chemistry, vol. 35, 1957, "The Reaction of Acetic and Trifluoroacetic Anhydrides with some Substituted Guanidine Hydrocholorides" Cockburn et al., pp. 1285–1292.
Journal of the Chemical Society, 1974, "Nitramines and Mitramides. Part XVII, Reactions with Dicyclohexylcarbodrimide", J.C.S. Perkins, pp. 956–960.
Chemical a Pharmaceutical Bulletin, vol. 32, No. 3, Mar. 1984, "Products of the Nitratin of 2–Thiazolylursas dnd 2–Thiazolythiourases", Yoda et al., pp. 3483–3492.
Derwent Publications Ltd., AU 8619–227–A, Ciba Geigy AG. 1989.
Chemical & PHarmaceutical Bulletin, vol. 23, 1975, "Pyridine Analogs of 1–Methyl–3–nitro–1–nitrosoguanidine and Related Compounds", Shozo Kamiya, pp. 2744–2748.
Moryia et al. "Structural modification of the 6–chloropyridyl moity in the imidacloprid skeleton" Biosci. Biotech. Biochem. 57:127:125(1983).
Moriya et al. "1–Diazinylmethyl–2–nitromethylene–and 2–nitorimino–imidazolines as new potential insecticides" J. Pesticide Sci. 18:119–123(1993).

*Primary Examiner*—C. Warren Ivy
*Assistant Examiner*—Lyman H. Smith
*Attorney, Agent, or Firm*—Foley & Lardner

[57] ABSTRACT

An insecticidal composition containing a guanidine derivative of the formula:

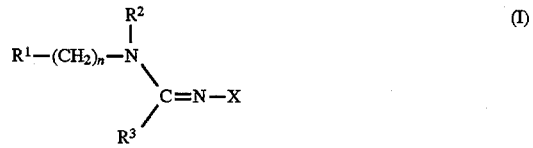

(I)

wherein $R^1$ is an optionally substituted homocyclic or heterocyclic group, n is 0 or 1, $R^2$ is a hydrogen atom or an optionally substituted hydrocarbon group, $R^3$ is a primary, secondary or tertiary amino group, X is an electron attractive group such as nitro or trifluoroacetyl group, provided that when n is 0, $R^1$ is an optionally substituted heterocyclic group or a salt thereof.

22 Claims, No Drawings

GUANIDINE DERIVATIVES THEIR PRODUCTION AND INSECTICIDES

This application is a divisional of application Ser. No. 08/091,744 (now U.S. Pat. No. 5,489,603), filed Jul. 15, 1993, which is a continuation of Ser. No. 07/707,916 filed May 30, 1991 (now abandoned), which is a divisional of Ser. No. 07/456,863 (now U.S. Pat. No. 5,034,404).

BACKGROUND OF THE INVENTION

1. Field of the Invention

The present invention relates to guanidine derivatives or salts thereof useful as insecticides, their production methods and insecticidal compositions containing the guanidine derivatives or salts thereof.

2. Prior Art

Various synthetic compounds possessing pest controlling effects have been used as insecticides. Most of the compounds belong to organic phosphates, carbamates, organic chlorine-containing compounds or pyrethroid compounds. It is well known that frequent use of such limited categories of compounds causes such harmful influence as increased resistance of pest insects which presently brings on public discussion at various places. Some compounds among the abovementioned insecticides exert potent insecticidal activities but show unsatisfactory effects on practical use, such as high toxicity on human beings, animals and fishes, eventual toxicity on enemies of pest insects and a high residual property in soil or the like.

On the other hand, with respect to guanidine derivatives or salts thereof, 3-nitro-1-(3-pyridylmethyl)guanidine, for example, is described in Chemical & Pharmaceutical Bulletin 23, 2744 (1975) and guanidine compounds possessing antiulcer activity such as cimetidine are reported in various articles or patents. However, there is no report of guanidine derivatives or salts thereof as insecticide.

SUMMARY OF THE INVENTION

Under such circumstances, the present invention is aimed to provide an insecticidal composition comprising a guanidine derivative or its salt which is low in toxicity on human beings, animals, fishes' and natural enemies of pest insects, besides safety and potent pest controlling effect and is useful in agricultural, horticultural and/or home gardening fields.

Thus, it provides (1) an insecticidal composition comprising a guanidine derivative of the formula (I)

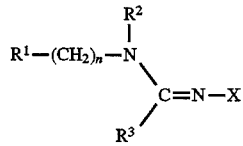

wherein $R^1$ is an optionally substituted homocyclic or heterocyclic group, n is 0 or 1, $R^2$ is a hydrogen atom or an optionally substituted hydrocarbon group, $R^3$ is a primary, secondary or tertiary amino group and X is an electron attractive group, provided that when n is 0, $R^1$ is an optionally substituted heterocyclic group, or salt thereof;

(2) a guanidine derivative of the formula ($I^a$)

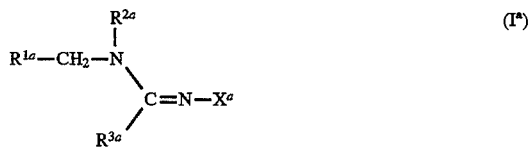

wherein $R^{1a}$ is an optionally substituted heterocyclic group, $R^{2a}$ is a hydrogen atom or an optionally substituted hydrocarbon group, $R^{3a}$ is a primary, secondary or tertiary amino group, provided that when $R^{2a}$ is a hydrogen atom, $R^{3a}$ is a secondary or tertiary amino group, and $X^a$ is a nitro group or trifluoroacetyl group, or salt thereof;

(3) a process for the preparation of the guanidine derivative ($I^a$) or salt thereof which comprises reacting a compound of the formula (II)

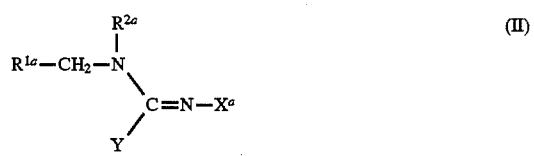

wherein $R^{1a}$, $R^{2a}$ and $X^a$ have the same meanings as defined above and Y is a leaving group, or salt thereof with ammonia, or a primary or secondary amine or salt thereof;

(4) a process for the preparation of the guanidine derivative ($I^a$) or salt thereof which comprises reacting a compound of the formula (III)

wherein the symbols have the same meanings as defined above, or salt thereof, with a compound of the formula (IV)

wherein the symbols have the same meanings as defined above, or salt thereof;

(5) a process for the preparation of the guanidine derivative ($I^a$) or salt thereof which comprises reacting a compound of the formula (V)

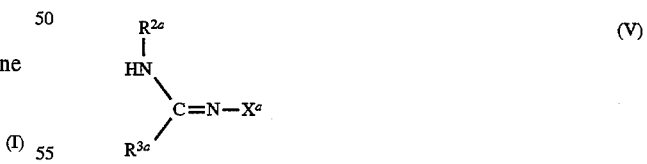

wherein the symbols have the same meanings as defined above, or salt thereof, with a compound of the formula (VI)

$$R^{1a}-CH_2-Y \qquad (VI)$$

wherein the symbols have the same meanings as defined above;

(6) a process for the preparation of the guanidine derivative ($I^a$) or salt thereof which comprises reacting a compound of the formula (VII)

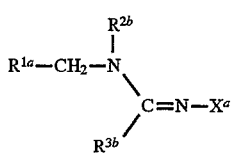

wherein $R^{1a}$ and $X^a$ have the same meanings as defined above, $R^{2b}$ is hydrogen atom or an optionally substituted hydrocarbon group, $R^{3b}$ is a primary, secondary or tertiary amino group, provided that when $R^{3b}$ is a tertiary amino group, $R^{2b}$ is a hydrogen atom, or salt thereof, with a compound of the formula (VIII)

$$Y-R \qquad (VIII)$$

wherein Y has the same meaning as defined above, and R is an optionally substituted hydrocarbon group, (7) a process for the preparation of the guanidine derivative ($I^a$) or salt thereof which comprises reacting a compound of the formula (IX)

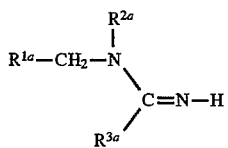

wherein the symbols have the same meanings as defined above, or salt thereof, with a compound of the formula (X)

$$Y-X^a \qquad (X)$$

wherein the symbols have the same meanings as defined above, or a nitrating agent.

In the above-mentioned formulae, $R^1$ denotes an optionally substituted homocyclic or heterocyclic group. The homocyclic or heterocyclic group of $R^1$ is a cyclic group containing the same atoms only or a cyclic group containing two or more different atoms, i.e., a cyclic hydrocarbon group or a heterocyclic group, respectively. $R^{1a}$ denotes an optionally substituted heterocyclic group, to which the definition of $R^1$ is applicable.

The cyclic hydrocarbon groups of $R^1$ include a $C_{3-8}$ cycloalkyl group such as cyclopropyl, cyclobutyl, cyclopentyl or cyclohexyl; a $C_{3-8}$ cycloalkenyl group such as cyclopropenyl, 1-cyclopentenyl, 1-cyclohexenyl, 2-cyclohexenyl, 1,4-cyclohexadienyl; and a $C_{6-14}$ aryl group such as phenyl, 1- or 2-naphthyl, 1-, 2- or 9-anthryl, 1-, 2-, 3-, 4- or 9-phenanthryl or 1-, 2-, 4-, 5- or 6-azulenyl. The preferred cyclic hydrocarbon groups are aromatic ones, e.g., $C_{6-14}$ aryl groups such as phenyl, etc.

The heterocyclic groups of $R^1$ or $R^{1a}$ include a 5-8-membered ring containing one to five hetero atoms of oxygen atom, sulfur atom and nitrogen atom and its condensed ring. Examples of the heterocyclic groups are 2- or 3-thienyl, 2- or 3-furyl, 2- or 3-pyrrolyl, 2-, 3- or 4-pyridyl, 2-, 4- or 5-oxazolyl, 2-, 4- or 5-thiazolyl, 3-, 4- or 5-pyrazolyl, 2-, 4- or 5-imidazolyl, 3-, 4- or 5-isoxazolyl, 3-, 4- or 5-isothiazolyl, 3- or 5-(1,2,4-oxadiazolyl), 1,3,4-oxadiazolyl, 3- or 5-(1,2,4-thiadiazolyl), 1,3,4-thiadiazolyl, 4- or 5-(1,2,3-thiadiazolyl), 1,2,5-thiadiazolyl, 1,2,3-triazolyl, 1,2,4-triazolyl, 1H- or 2H-tetrazolyl, N-oxido-2-, 3- or 4-pyridyl, 2-, 4- or 5-pyrimidinyl, N-oxido-2-, 4- or 5-pyrimidinyl, 3- or 4-pyridazinyl, pyrazinyl, N-oxido-3- or 4-pyridazinyl, benzofuryl, benzothiazolyl, benzoxazolyl, triazinyl, oxotriazinyl, tetrazolo[1,5-b]pyridazinyl, triazolo[4,5-b]pyridazinyl, oxoimidazinyl, dioxotriazinyl, pyrrolidinyl, piperidinyl, pyranyl, thiopyranyl, 1,4-oxazinyl, morpholinyl, 1,4-thiazinyl, 1,3-thiazinyl, piperazinyl, benzoimidazolyl, quinolyl, isoquinolyl, cinnolinyl, phthalazinyl, quinazolinyl, quinoxalinyl, indolizinyl, quinolizinyl, 1,8-naphthyridinyl, purinyl, pteridinyl, dibenzofuranyl, carbazolyl, acridinyl, phenanthridinyl, phenazinyl, phenothiazinyl or phenoxazinyl. The preferred heterocyclic groups are 5- or 6-membered nitrogen-containing heterocyclic groups such as 2-, 3- or 4-pyridyl or 2-, 4- or 5-thiazolyl. The homocyclic or heterocyclic groups of $R^1$ and the heterocyclic groups of $R^{1a}$ may possess one to five (preferably one) substituents which are the same or different. Examples of the substituents are a $C_{1-15}$ alkyl group such as methyl, ethyl, propyl, isopropyl, butyl, isobutyl, s-butyl, t-butyl, pentyl, hexyl, heptyl, octyl, nonyl, decyl, undecyl, dodecyl, tridecyl, tetradecyl or pentadecyl; a $C_{3-10}$ cycloalkyl group such as cyclopropyl, cyclobutyl, cyclopentyl or cyclohexyl; a $C_{2-10}$ alkenyl group such as vinyl, allyl, 2-methylallyl, 2-butenyl, 3-butenyl or 3-octenyl; a $C_{2-10}$ alkynyl group such as ethynyl, 2-propynyl or 3-hexynyl; a $C_{3-10}$ cycloalkenyl group such as cyclopropenyl, cyclopentenyl or cyclohexenyl; a $C_{6-10}$ aryl group such as phenyl or naphthyl; a $C_{7-10}$ aralkyl group such as benzyl or phenylethyl; nitro group; hydroxy group; mercapto group; oxo group; thioxo group; cyano group; carbamoyl group; carboxyl group; a $C_{1-4}$ alkoxycarbonyl group such as methoxycarbonyl or ethoxycarbonyl; sulfo group; a halogen atom such as fluorine, chlorine, bromine or iodine; a $C_{1-4}$ alkoxy group such as methoxy, ethoxy, propoxy, isoporpoxy, butoxy, isobutoxy, s-butoxy or t-butoxy; a $C_{6-10}$ aryloxy group such as phenoxy; a $C_{1-4}$ alkylthio group such as methylthio, ethylthio, n-propylthio, isopropylthio, n-butylthio or t-butylthio; a $C_{6-10}$ arylthio group such as phenylthio; a $C_{1-4}$ alkylsulfinyl group such as methylsulfinyl or ethylsulfinyl; a $C_{6-10}$ arylsulfinyl group such as phenylsulfinyl; a $C_{1-4}$ alkylsulfonyl group such as methylsulfonyl or ethylsulfonyl; a $C_{6-10}$ arylsulfonyl group such as phenylsulfonyl; amino group; a $C_{2-6}$ acylamino group such as acetylamino or propionylamino; a mono- or di-$C_{1-4}$ alkylamino group such as methylamino, ethylamino, n-propylamino, isopropylamino, n-butylamino, dimethylamino or diethylamino; a $C_{3-6}$ cycloalkylamino group such as cyclohexylamino; a $C_{6-10}$ arylamino group such as anilino; a $C_{2-4}$ acyl such as acetyl; a $C_{6-10}$ arylcarbonyl group such as benzoyl; and a 5- or 6-membered heterocyclic group containing one to four hetero atoms selected from oxygen, sulfur and nitrogen, such as 2- or 3-thienyl, 2- or 3-furyl, 3-, 4- or 5-pyrazolyl, 2-, 4- or 5-thiazolyl, 3-, 4- or 5-isothiazolyl, 2-, 4- or 5-oxazolyl, 3-, 4- or 5-isoxazolyl, 2-, 4- or 5-imidazolyl, 1,2,3- or 1,2,4-triazolyl, 1H- or 2H-tetrazolyl, 2-, 3- or 4-pyridyl, 2-, 4- or 5-pyrimidinyl, 3- or 4-pyridazinyl, quinolyl, isoquinolyl or indolyl. One to five substituents selected from the above exemplified substituents can carry on the above-mentioned homocyclic or heterocyclic groups. When the substituent is e.g., the $C_{6-10}$ aryl, $C_{7-10}$ aralkyl, $C_{3-10}$ cycloalkyl, $C_{3-10}$ cycloalkenyl, $C_{6-10}$ aryloxy, $C_{6-10}$ arylthio, $C_{6-10}$ arylsulfinyl, $C_{6-10}$ arylsulfonyl, $C_{6-10}$ arylamino or heterocyclic group, it may be further substituted by one to five of the above-mentioned halogen atom; hydroxy group; $C_{1-4}$ alkyl group such as methyl, ethyl, propyl, isopropyl, butyl, isobutyl, s-butyl or t-butyl; $C_{2-4}$ alkenyl group such as vinyl, allyl or 2-methylallyl; $C_{2-4}$ alkynyl group such as ethynyl or 2-propynyl; $C_{6-10}$ aryl group; $C_{1-4}$ alkoxy group; phenoxy group; $C_{1-4}$ alkylthio group or phenylthio group. When the substituent is the $C_{1-15}$ alkyl, $C_{2-10}$ alkenyl, $C_{2-10}$ alkynyl, $C_{1-4}$ alkoxy, $C_{1-14}$ alkylthio, $C_{1-4}$ alkylsulfinyl, $C_{1-4}$ alkylsulfonyl, amino, mono- or di-$C_{1-4}$ alkylamino, $C_{3-6}$ cycloalkylamino or $C_{6-10}$ arylamino group, it may be further substituted by one to five of the above-mentioned halogen atom, hydroxy group, $C_{1-4}$ alkoxy group or $C_{1-4}$ alkylthio group.

Preferred examples of $R^1$ are 5- or 6-membered nitrogen-containing heterocyclic groups such as pyridyl or thiazolyl which may be substituted by one or two halogens.

The symbol "n" denotes 0 or 1, preferably 1.

The hydrocarbon group in the "optionally substituted hydrocarbon group" of $R^2$, $R^{2a}$, $R^{2b}$ and R includes the $C_{1-15}$ alkyl, $C_{3-10}$ cycloalkyl, $C_{2-10}$ alkenyl, $C_{2-10}$ alkynyl, $C_{3-10}$ cycloalkenyl, $C_{6-10}$ aryl and $C_{7-10}$ aralkyl groups which are mentioned with respect to $R^1$. Those mentioned as the substituents on the homocyclic or heterocyclic group of $R^1$ are applicable to the substituents on the "optionally substituted hydrocarbon group".

Preferred examples of $R^2$, $R^{2a}$ and $R^{2b}$ are hydrogen atom and a $C_{1-4}$ alkyl group such as methyl, ethyl or propyl. Preferred example of R is the above-mentioned $C_{1-4}$ alkyl group.

$R^3$, $R^{3a}$ and $R^{3b}$ denote a primary, secondary or tertiary amino group, which can be represented by the formula:

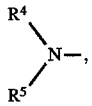

wherein $R^4$ and $R^5$ are, the same or different, a hydrogen atom or an optionally substituted hydrocarbon group or both $R^4$ and $R^5$ are combined with the adjacent nitrogen atom to form a cyclic amino group. (Here, the primary amino group is an unsubstituted amino group in case where $R^4$ and $R^5$ of the above formula are a hydrogen atom, the secondary amino group is mono-substituted amino group in case where either one of $R^4$ and $R^5$ is hydrogen atom and the tertiary amino group is disubstituted amino group in case where both of $R^4$ and $R^5$ are not hydrogen atom.) The optionally substituted hydrocarbon groups mentioned with respect to $R^2$, $R^{2a}$, $R^{2b}$ and R are applicable to those of $R^4$ and $R^5$.

Examples of the cyclic amino groups which are formed from $R^4$ and $R^5$ together with the adjacent nitrogen atom are aziridino, azetidino, pyrrolidino, morpholino and thiomorpholino groups. Preferred examples of $R^3$, $R^{3a}$ and $R^{3b}$ are an unsubstituted amino group; a mono-$C_{1-4}$ alkylamino group such as methylamino, ethylamino or propylamino; a di-$C_{1-4}$ alkylamino group such as dimethylamino or ethylmethylamino and a $C_{1-4}$ acylamino group such as formamido, N-methylformamido or acetamido.

Examples of the electron attractive groups of X are cyano, nitro, an alkoxycarbonyl (e.g., $C_{1-4}$ alkoxycarbonyl such as methoxycarbonyl or ethoxycarbonyl), hydroxycarbonyl, a $C_{6-10}$ aryloxycarbonyl (e.g., phenoxycarbonyl), a heterocycle-oxycarbonyl (the abovementioned heterocycle group being applicable to this group, thus specifically pyridyloxycarbonyl or thienyloxycarbonyl), a $C_{1-4}$ alkylsulfonyl which may be substituted by a halogen such as chlorine, bromine or fluorine (e.g., methylsulfonyl, trifluoromethylsulfonyl, ethylsulfonyl), sulfamoyl, a di-$C_{1-4}$ alkoxyphosphoryl (e.g., diethoxyphosphoryl), a $C_{1-4}$ acyl which may be substituted by a halogen such as chlorine, bromine or fluorine (e.g., acetyl, trichloroacetyl or trifluoroacetyl), $C_{6-10}$ aryl-carbonyl (e.g., benzoyl), carbamoyl or a $C_{1-4}$ alkylsulfonylthiocarbamoyl (e.g., methylsulfonylthiocarbamoyl). Preferred example of the electron attractive group is a nitro group. $X^a$ denotes a nitro or trifluoroacetyl group.

Examples of the leaving groups of Y are a halogen atom such as chlorine, bromine, iodine or fluorine; a $C_{1-4}$ alkylsulfonyloxy group which may be substituted by one to three halogen atoms (e.g., Cl, Br or F) such as methanesulfonyloxy, ethanesulfonyloxy, butanesulfonyloxy or trifluoromethanesulfonyloxy; a $C_{6-10}$ arylsulfonyloxy group which may be substituted by one to four halogen atoms (e.g., Cl, Br or F) such as benzenesulfonyloxy, p-toluenesulfonyloxy, p-bromobenzenesulfonyloxy or mesitylenesulfonyloxy; a $C_{1-6}$ acyloxy group which may be substituted by one to three halogen atoms(e.g., Cl, Br or F) such as acetyloxy, propionyloxy or trifluoroacetyloxy; a $C_{6-10}$ arylcarbonyloxy group such as benzoyloxy; hydroxy group; a $C_{1-4}$ alkoxy group such as methoxy or ethoxy; a $C_{1-4}$ alkylthio group such as methylthio or ethylthio; a $C_{1-4}$ alkylsulfinyl group such as methylsulfinyl; a $C_{1-4}$ alkylsulfonyl group such as methylsulfonyl; a $C_{6-10}$ aryloxy group which may be substituted by one to three of a halogen (e.g., Cl, Br or F) or nitro, such as phenoxy, p-chlorophenoxy or p-nitrophenoxy; a heterocycleoxy group such as 2-pyridyloxy or 2-benzoxazolyloxy; a $C_{6-10}$ arylthio group which may be substituted by one or two of nitro or the like such as phenylthio or p-nitrophenylthio; a $C_{7-12}$ aralkylthio group which may be substituted by one or two of nitro or the like such as benzylthio or p-nitrobenzylthio; a heterocyclethio group such as 2-pyridylthio or 2-benzothiazolylthio; amino group; a mono- or di-$C_{1-4}$ alkylamino group such as methylamino, ethylamino or dimethylamino and a 5-membered nitrogen-containing heterocycle group such as 1-imidazolyl or 1,2,4-triazol-1-yl.

Preferred examples of Y in the compounds (II) and (III) are a $C_{1-4}$ alkylthio group such as methylthio or ethylthio, a $C_{7-12}$ aralkylthio group such as benzylthio, a $C_{1-4}$ alkoxy group such as methoxy or ethoxy, amino group and a mono- or di-$C_{1-4}$ alkylamino group such as methylamino, ethylamino or dimethylamino. Those of Y in the compounds (VI), (VIII) and (X) are a halogen atom such as chlorine or bromine, a $C_{1-4}$ alkylsulfohyloxy group which may be substituted by one to three halogen atoms such as methanesulfonyloxy or trifluoromethanesulfonyloxy, a $C_{6-10}$ arylsulfonyloxy group such as benzenesulfonyloxy or p-toluenensulfonyloxy, hydroxyl group and a $C_{1-4}$ acyloxy group which may be substituted by one to three halogen atoms such as acetyloxy or trifluoroacetyloxy.

Preferred example of the guanidine derivative (I) or its salt is the compound of the formula ($I^b$)

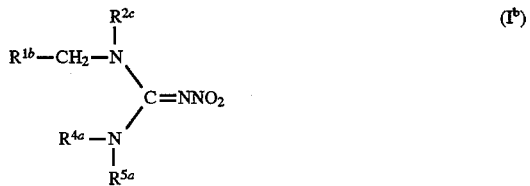

wherein $R^{1b}$ is a pyridyl, a halogenopyridyl or halogenothiazolyl group, $R^{2c}$, $R^{4a}$ and $R^{5a}$ are the same or different, hydrogen atom, or a methyl, ethyl, formyl or acetyl group, or its salt. Specifically, $R^{1b}$ of the formula ($I^b$) includes 3-pyridyl, a halogenopyridyl such as 6-chloro-3-pyridyl, 6-bromo-3-pyridyl or 5-bromo-3-pyridyl or a halogenothiazolyl such as 2-chloro-5-thiazolyl or 2-bromo-5-thiazolyl.

The guanidine derivatives (I) or their salts form cis and trans-isomers with respect to the position of X and also can theorethically form tautomers in the case of $R^2$ being hydrogen or $R^3$ being primary or secondary amino. These isomers of the guanidine derivatives (I) or their salts are included in the present invention.

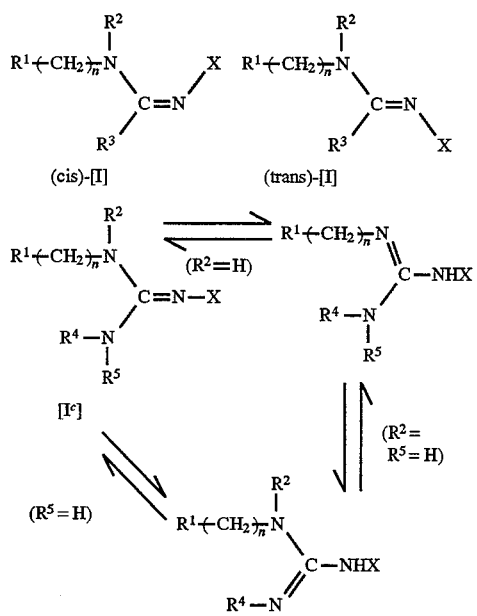

In the above formulae, the symbols have the same meanings as defined above.

Examples of the salts of the guanidine derivatives (I), (I$^a$) and (I$^b$) are the salts with an inorganic acid such as hydrochloric acid, hydrobromic acid, hydroiodic acid, phosphoric acid, sulfuric acid or perchloric acid, or an organic acid such as formic acid, acetic acid, tartaric acid, malic acid, citric acid, oxalic acid, succinic acid, benzoic acid, picric acid or p-toluenesulfonic acid.

The guanidine derivatives (I) or their salts can be used as insecticide in any application form suited for general agricultural chemicals. That is, one, two, or more than two kinds of the compounds (I) or their salts are used in the form of preparation such as emulsifiable concentrates, oil solution, wettable powders, dusts, granules, tablets, sprays or ointment, according to the purpose of use, by dissolving or dispersing them in suitable liquid carriers, or mixing them with or absorbing them on suitable solid carriers. These preparations may contain, if necessary, emulsifying agent, suspending agent, spreading agent, penetrating agent, wetting agent, thickening agent or stabilizer, and can be prepared by any conventional method known per se.

The rate of the compound (I) or a salt thereof contained in an insecticidal preparation is suitably about 10 to 90% by weight in the case of emulsifiable concentrates or wettable powders, about 0.1 to 10% by weight in the case of oil solution or dusts and about 1 to 20% by weight in the case of granules. However, such concentration may be changed properly, depending on the purpose of use. Emulsifiable concentrates, wettable powders or the like is suitably diluted or extended (for example, to 100 to 100000 times) with water or the like, on the occasion of use, and then scattered.

Suitable examples of the liquid carriers (solvents) include solvents such as water, alcohols (for example, methanol, ethanol, n-propanol, isopropanol or ethylene glycol), ketones (for example, acetone or methyl ethyl ketone), ethers (for example, dioxane, tetrahydrofuran, ethylene glycol monomethyl ether, diethylene glycol monomethyl ether or propylene glycol monomethyl ether), aliphatic hydrocarbons (for example, kerosine, kerosene oil, fuel oil or machine oil), aromatic hydrocarbons (for example, benzene, toluene, xylene, solvent naphtha or methylnaphthalene), halogenated hydrocarbons (for example, dichloromethane, chloroform or carbon tetrachloride), acid amides (for example, dimethylformamide or dimethylacetamide), esters (for example, ethyl acetate, butyl acetate or fatty acid glycerol ester) or nitriles (for example, acetonitrile or propionitrile). These solvents are used individually or as a suitable mixture of two, or more, of them.

Suitable examples of the solid carriers (diluents or dust carrier) include vegetable powder (for example, soybean meal, tobacco meal, wheat flour or wood flour), mineral powders (for example, clays such as kaolin, bentonite, or acid clay, talcs such as talc powder or pyrophyllite powder), silicas (for example, diatomaceous earth or mica powder), aluminas, sulfur powder or active carbon. They are used individually or as a suitable mixture of two, or more, of them.

Also, suitable examples of bases for ointments include polyethylene glycol, pectin, polyalcohol esters of higher aliphatic acids (for example, glycerin monostearate), cellulose derivatives (for example, methyl cellulose), sodium alginate, bentonite, higher alcohols, polyalcohols (for example, glycerin), vaseline, white petrolatum, liquid paraffin, lard, various vegetable oils, lanolin, dehydrated lanolin, hard oil or resins. They are used individually, or as a suitable mixture of two, or more, of them or together with surface active agents mentioned below.

As surface active agents used as the emulsifying agent, spreading agent, penetrating agent or dispersing agent, nonionic or anionic surface active agents such as soaps; polyoxyethylene alkyl aryl ethers (e.g., Noigen® and EA 142® from Dai-ichi Kogyo Seiyaku K.K., Japan, and Nonal® from Toho Chemical, Japan); alkyl sulfates (e.g., Emal 10® and Emal 40® from Kao K.K., Japan); alkyl sulfonates (e.g., Neogen® and Neogen T® from Dai-ichi Kogyo Seiyaku K.K., and Neopelle® from Kao K.K.); polyethylene glycol ethers (e.g., Nonipol 85®, Nonipol 10®, Nonipol 160® from Sanyo Kasei K.K., Japan); or polyhydric alcohol esters (e.g., Tween 20® and Tween 80® from Kao K.K.) are used, if necessary.

The guanidine derivatives (I) or their salts can also be used, as occasion demands, in combination with or as an admixture with other insecticides (for example, pyrethroid insecticides, organophosphorus insecticides, carbamate insecticides or natural insecticides), acaricides, nematicides, herbicides, plant hormones, plant growth regulators, fungicides (for example, copper fungicides, organic chlorine fungicides, organic sulfur fungicides or phenol fungicides), synergistic agents, attractants, repellents, pigments and/or fertilizers.

The guanidine derivatives (I) or their salts are effective in preventing sanitary or horticultural insect pests and animal and plant parasites and can exert potent insecticidal activities when they are directly contacted with insects, e.g., by applying to their living animals or plants. An interesting characteristic property of the compounds is found in that potent insecticidal activities can be achieved by once absorbing the compounds in plants through their root, leave or stem which are then sucked or bitten by insects or contacted with insects. Such property is advantageous for preventing suctorial type or mandible type insecticides. Moreover, the compounds (I) and their salts possess safe and advantageous properties as agents for preventing agricultural injurious insects, such as no substantial damage on plants and less toxicity against fishes.

Specifically, the preparations containing the guanidine derivatives (I) or their salts are especially effective in preventing Hemiptera injuricus insects such as *Eurydema rugosum, Scotinophara lurida, Riptortus clavatus, Stephanitis nashi, Laodelphax striatellus, Nilaparvata lugens,*

*Nephotettix cincticeps, Unaspis yanonensis, Aphis glycines, Lipaphis erysimi, Brevicoryne brassicae, Aphis gossypii*; Lepidoptera injurious insects such as *Spodoptera litura, Plutella xylostella, Pieris rapae crucivora, Chilo suppressalis, Autographa nigrisigna, Helicoverpa assulta, Pseudaletia separata, Mamestra brassicae, Adoxophyes orana fasciata, Notarcha derogata, Cnaphalocrocis medinalis, Phthorimaea operculella*; Coleoptera injurious insects such as *Epilachna vigintioctopunctata, Aulacophora femoralis, Phyllotreta striotata, Oulema oryzae, Echinocnemus squameus*; Diptera injurious insects such as *Musca domestica, Culex pipiens pallens, Tabanus trigonus, Delia antiqua, Delia platura*; Orthosptera injurious insects such as *Locusta migratoria, Gryllotalpa africana*; Dictyoptera injurious insects such as *Blattella germanica, Periplaneta fuliginosa*; Tetranychidaes such as *Tetranychus urticae, Panonychus citri, Tetranychus kanzawai, Tetranychus cinnabarinus, Panonychus ulmi, Aculops pelekassi*; and Nematodes such as *Aphelenchoides besseyi*.

The insecticidal composition comprising the quanidine derivative (I) or its salt of the present invention is an excellent agricultural product having fairly low toxicity and good safety. It can be used in a similar way to the conventional insecticidal composition and can exert excellent effects in comparison with the conventional composition. For example, the insecticidal composition of the present invention can be applied to the target insects, by treatment in nursery box, application for stem and leaf of crop, spraying for insects, application in water of a paddy field or soil treatment of a paddy field. The amount of application may broadly vary depending on the season, place and method of application, and so forth. However, the active ingredient (the guanidine derivative (I) or its salt) is used in general, in an amount of 0.3 g to 3,000 g, preferably 50 g to 1,000 g per hectare. When the insecticidal composition of the present invention is in a wettable powder, it can be used by diluting it so as to be 0.1–1000 ppm, preferably 10–500 ppm as the final concentration of the active ingredient.

The guanidine derivatives ($I^a$) or salts thereof can be prepared by Methods (A)–(F) mentioned below. Besides, when the compound ($I^a$) is obtained in its free form or salt form, it can be converted into the corresponding salt (already mentioned salt form) or free form by the conventional methods. Also, any compound of the compounds ($I^a$) may be in any of free or salt form when it is used as a raw material for preparing another compound of the compounds ($I^a$). Other raw materials than the compounds ($I^a$) which can form salts can be employed as any of free or salt form. Accordingly, raw materials to be employed and products in the below-mentioned Methods include their respective salts [e.g., salts with the acids as mentioned in the compound (I)].

(A) In the present invention, the guanidine derivative ($I^a$) or its salt can be prepared by reacting a compound (II) or its salt with ammonia, a primary or secondary amine or its salt.

The ammonia, primary or secondary amines or salts thereof to be employed are amines represented by the formula $$R^{3a}-H \quad (XI)$$

wherein $R^{3a}$ has the same meaning as defined above, or salts thereof. In the reaction, it is especially preferred to use the compound (II) in which Y is a $C_{1-4}$alkylthio such as methylthio, or amino. The compound (XI) or its salt is preferably employed in about 0.8–2.0 equivalents, to the compound (II) or its salt but may be employed in about 2.0–20 equivalents as far as the reaction is not impeded.

The reaction is usually conducted in a suitable solvent, although it may be conducted without solvent. Examples of the solvents are water, alcohols such as methanol, ethanol, n-propanol or isopropanol; aromatic hydrocarbons such as benzene, toluene or xylene; halogenated hydrocarbons such as dichloromethane or chloroform; saturated hydrocarbons such as hexane, heptane or cyclohexane; ethers such as diethyl ether, tetrahydrofuran (hereinafter abbreviated as THF) or dioxane; ketones such as acetone; nitriles such as acetonitrile; sulfoxides such as dimethylsulfoxide (hereinafter abbreviated as DMSO); acid amides such as dimethylformamide (hereinafter abbreviated as DMF), esters such as ethyl acetate or carboxylic acids such as acetic acid or propionic acid. These solvents can be used singly or in admixture of two or more kinds, in an appropriate ratio such as 1:1–1:10. When the reaction mixture is not homogenous, the reaction may be conducted in the presence of a phase transfer catalyst such as a quaternary ammonium salt (e.g., triethylbenzylammonium chloride, tri-n-octylmethylammonium chloride, trimethyldecylammonium chloride, tetramethylammonium bromide) or crown ethers.

The reaction may be accelerated by addition of a base or metallic salt in an amount of 0.01–10 equivalents, preferably 0.1–3 equivalents. Examples of the bases are inorganic bases such as sodium hydrogen carbonate, potassium hydrogen carbonate, sodium carbonate, potassium carbonate, sodium hydroxide, potassium hydroxide, calcium hydroxide, phenyl lithium, butyl lithium, sodium hydride, potassium hydride, sodium methoxide, sodium ethoxide, metallic sodium or metallic potassium; and organic bases such as triethylamine, tributylamine, N,N-dimethylaniline, pyridine, lutidine, collidine, 4-(dimethylamino) pyridine or DBU (1,8-diazabicyclo[5,4,0]undecene-7). The above organic bases themselves can be used as a solvent, too. Examples of the metallic salts are copper salts such as copper chloride, copper bromide, copper acetate or copper sulfate; or mercury salts such as mercury chloride, mercury nitrate or mercury acetate.

Usually, the reaction temperature is in the range of −20° C. to 150° C., preferably 0° C. to 100° C. and the reaction time is 10 minutes to 50 hours, preferably 1 to 20 hours.

(B) The compound ($I^a$) or its salt can be prepared by reacting a raw material (III) or its salt with a compound (IV) or its salt.

Preferred examples of Y and the reaction conditions are the same as those stated in Method (A).

(C) The compound ($I^a$) or its salt can be also prepared by reacting a compound (V) or its salt with a compound (VI).

The leaving group represented by Y of the compound (VI) is preferably a halogen such as chlorine or bromine; a $C_{1-4}$ alkylsulfonyloxy such as methanesulfonyloxy; a $C_{6-10}$ arylsulfonyloxy such as p-toluenesulfonyloxy; or a $C_{1-4}$ acyloxy which may be substituted by one to three halogens such as acetyloxy or trifluoroacetyloxy.

The compound (VI) is preferably used in about 0.8–1.5 equivalents, to the compound (V), although a large excess amount may be used as far as it does not impede the reaction. In order to accelerate the reaction, it may be conducted in the presence of a base, to which those stated in Method (A) are applicable. The base can be used in about 0.5 equivalents to a large excess amount, preferably about 0.8 to 1.5 equivalents, to the compound (V). The organic base when used as the base can serve as the solvent, too.

The reaction is preferably conducted in a solvent as mentioned in Method (A) and if the reaction system is not homogenous, may be conducted in the presence of a phase-transfer catalyst as mentioned in Method (A). The reaction temperature is usually in the range of −20° C.–150° C., preferably 0° C.–80° C. The reaction time is usually in the range of 10 minutes to 50 hours, preferably 2 hours–20 hours.

(D) The compound ($I^a$) or its salt can be prepared by reacting a compound (VII) or its salt with a compound (VIII).

In the reaction, preferred examples of Y and the reaction conditions are the same as those stated in Method (C).

(E) The compound ($I^a$) or its salt can be prepared by reacting a compound (IX) or its salt with a compound (x).

In the reaction, preferred examples of Y are a halogen such as bromine or chlorine; or a $C_{1-4}$ acyloxy which may be substituted by one to three halogens such as acetyloxy or trifluoroacetyloxy. The reaction can be conducted under the same condition as stated in Method (C).

The compound ($I^a$) in which $X^a$ is nitro, i.e., which can be represented by the formula

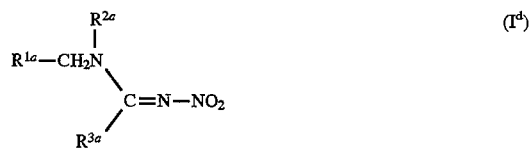

($I^d$)

wherein $R^{1a}$, $R^{2a}$ and $R^{3a}$ have the same meanings as defined above, or salt thereof can be prepared by any of Method (A)–(E) as stated above but also prepared by the following method.

(F) The compound ($I^a$) or its salt can be prepared by nitrating a compound (IX) or its salt.

60–100% nitric acid is frequently used as a nitrating agent. Other nitrating agents such as an alkali metal nitrate (e.g., sodium nitrate or potassium nitrate), an alkyl nitrate (e.g., ethyl nitrate or amyl nitrate), nitronium tetrafluoroborate ($NO_2BF_4$) or nitronium trifluoromethanesulfonate ($NO_2CF_3SO_3$) may be used.

The nitrating agent can be used in 1.0–20 equivalents to the compound (IX) or its salt, preferably 2.0–10 equivalents in the case of nitric acid.

The reaction may be conducted without any solvent but is usually conducted in sulfuric acid, acetic acid, acetic anhydride, trifluoroacetic anhydride or trifluoromethanesulfonic acid as the solvent. Depending upon circumstances, the solvents mentioned in Method (A) or mixture thereof can be used. The reaction temperature is in the range of −50° C. to 100° C., preferably −20° C. to 60° C. and the reaction time is 10 minutes to 10 hours, preferably 30 minutes to 2 hours.

The compound ($I^a$) or its salt thus obtained can be isolated and purified, e.g., by a conventional method such as concentration, concentration under reduced pressure, distillation, fractional distillation, extraction by solvent, change of basicity, redistribution, chromatography, crystallization, recrystallization or the like.

The compounds (II) and (III) or salts thereof to be employed as the raw materials of the methods in the present invention are partially known and can be prepared e.g., by the methods described in *J. Med. Chem.* 20, 901 (1977), Chem. Pharm. Bull. 23, 2744 (1975) and GB-A-2,201,596 or analogues methods thereto.

The primary or secondary amines (XI) [to be employed in the above-mentioned Method (A)], the compounds (IV) or their salts can be prepared by the methods described in e.g., "SHIN JIKENKAGAKU KOZA (New Experimental Chemistry Handbook)" issued by Maruzen Publishing Co., Ltd. of Japan, Vol. 14-III, pp. 1332–1339 and analogues ones thereto.

The compound (V) and (IX) or their salts can be prepared by the methods described in e.g., Rodd's Chemistry of Carbon Compounds, Vol. 1, Part C, pp. 341–353 or *Chemical Reviews*, 51, 301(1952) and analogous ones thereto. The compounds (VII) or their salts can be prepared e.g., by any of Methods (A), (B), (C), (E) and (F), because they are included in the compounds ($I^a$) or their salts.

The compounds (VI), (VIII) and (X) can be prepared by the methods described in "SHIN JIKENKAGAKU KOZA (New Experimental Chemistry Handbook)" issued by Maruzen Publishing Co., Ltd. of Japan, Vol. 14-I, pp. 307–450 and Vol. 14-II, pp. 1104–1133 or analogues method thereto.

Activity

As will be clear from the following tests, the guanidine derivatives (I) and salts thereof possess excellent insecticidal activities.

Test Example 1 (Effect against *Nilaparvata lugens*)

5 mg of each of test compounds (shown by Compound No. obtained in Example as stated hereinafter) was dissolved in 0.5 ml of acetone containing Tween 20® and diluted to a predetermined concentration (500 ppm) by addition of Dyne (a spreader produced by Takeda Chemical Industries, Ltd. of Japan) diluted 3000 times with water. The solution at a rate of 10 ml/pot was sprayed on leaf and stem of rice seedlings at the second leaf stage raised in a nursery box. The treated rice seedlings were put into a test tube containing water at the bottom, to which 10 larvae at 3 instar of *Nilaparvata lugens* were released. After being sealed with an aluminum stopper, the test tube was kept in an incubator adjusted to 25° C. Death number was counted 7 days after release. The mortality rate was calculated by the following formula and shown in Table 1.

$$\text{Mortality (\%)} = \frac{\text{the number of dead insects}}{\text{the number of insects released}} \times 100$$

TABLE 1

| Compound No. | Mortality (%) |
|---|---|
| 1 | 100 |
| 2 | 100 |
| 3 | 100 |
| 4 | 100 |
| 5 | 100 |
| 6 | 100 |
| 7 | 100 |
| 8 | 100 |
| 9 | 100 |
| 10 | 100 |
| 11 | 100 |
| 12 | 100 |
| 13 | 100 |
| 14 | 100 |
| 15 | 100 |
| 16 | 100 |
| 17 | 100 |
| 18 | 100 |
| 19 | 100 |
| 20 | 100 |
| 21 | 100 |
| 22 | 100 |
| 23 | 100 |
| 24 | 100 |
| 25 | 100 |
| 26 | 100 |
| 27 | 100 |
| 28 | 100 |
| 29 | 100 |
| 30 | 100 |
| 31 | 100 |
| 32 | 100 |
| 33 | 100 |
| 34 | 100 |

Table 1 clearly reveals that the guanidine derivatives (I) or salts thereof have an excellent insecticidal effect on *Nilaparvata lugens*.

Test Example 2 (Effect on *Spodoptera litura*)

1 mg of each of test compounds (shown by Compound No. of Example as mentioned below) was dissolved in 0.5 ml of acetone containing Tween 20® and diluted to a predetermined concentration (500 ppm) by addition of 3000 folds diluted Dyne-water. The solution at a rate of 20 ml/pot was sprayed on a soy seedling at the simple leaf unfolding stage. After the solution having dried, two simple leaves of the soy seedling were cut off and put into an ice cream cup, to which 10 larvae at 3 instar of *Spodoptera litura* were released. After released, the cup was kept in an incubator adjusted to 25° C. Death number was counted 2 days after release. The mortality rate was calculated by the formula written in Test Example 1, and shown in Table 2.

TABLE 2

| Compound No. | Mortality (%) |
|---|---|
| 5 | 100 |
| 7 | 100 |
| 16 | 100 |
| 18 | 100 |
| 19 | 100 |
| 23 | 100 |
| 25 | 100 |
| 26 | 100 |
| 27 | 100 |
| 31 | 100 |

Table 2 proves that the guanidine derivatives (I) or salts thereof have an excellent insecticidal effect on *Spodoptera litura*.

Examples p This invention is illustrated in further detail in the Reference Examples and Examples, which are only examples, and do not limit this invention. Modifications within the scope of this invention are permissible.

Elution in a column chromatography in the Reference Examples, and Examples was conducted while monitoring with TLC (Thin Layer Chromatography). In the TLC monitoring, the TLC plate used was Kieselgel® 60$F_{254}$ manufactured by Merck Co. (70–230 mesh), the developing solvent was the same as the one used for eluting in the column chromatography, and the detection was conducted with a UV detector. The silica gel for the column was Kieselgel 60 manufactured by Merck Co. (West Germany) (70–230 mesh). NMR spectra indicate $^1$H-NMR and were measured using tetramethylsilane as an internal standard with a spectrometer Varian EM390 (90 MHz) and all δ values are expressed in ppm. The value shown in () for a mixed solvent as the developing solvent is a mixing ratio in volume of constituent solvents. The abbreviations used in examples and Table 3 have the following meanings.

Me: methyl group
Et: ethyl group
ph: phenyl group
s: singlet
br: broad
d: doublet
t: triplet
q: quartet
m: multiplet
dd: doublet of doublets
J: coupling constant
Hz: Hertz
CDCl$_3$: deutero-chloroform
DNSO-d$_6$: deutero-dimethylsulfoxide
%: percentage by weight
m.p.: melting point Further, room temperature means 15°–20° C., and all of melting points and temperature were shown on the centigrade.

Reference Example 1

A mixture of 70.3 g of 2-chloro-5-(hydroxymethyl) pyridine and 50 ml of 1,2-dichloroethane was dropwise added to a mixture of 87.4 g of thionyl chloride and 100 ml of 1,2-dichloroethane during 30 minutes in a water bath of 5°–20° C. The mixture was stirred for an hour and a half at room temperature and for 4 hours and a half under refluxing. After concentrating, to the residue were added 200 ml of chloroform and 60 ml of water and then added portionwise 20 g of sodium hydrogen carbonate under stirring. The organic phase was separated, treated with active carbon and concentrated to obtain 75.9 g of 2-chloro-5-(chloromethyl) pyridine as a yellowish brown solid.

$^1$H NMR(CDCl$_3$): 4.57(2H,s), 7.34(1H,d,J=8.5 Hz), 7.72 (1H,dd,J=8.5, 2.5 Hz), 8.40(1H,d,J=2.5 Hz)

By the same method, 5-(chloromethyl)thiazole, 5-chloromethyl-2-methylthiazole and 5-chloromethyl-2-phenylthiazole were obtained.

Reference Example 2

A mixture of 14.99 g of 2-chloro-5-(chloromethyl) pyridine, 63.01 g of 25% ammonia water and 60 ml of acetonitrile in a stainless steel autoclave was stirred for 2 hours in an oil bath of 80° C. After adding 12.3 g of 30% sodium hydroxide aqueous solution, the reaction mixture was concentrated. The residue to which 200 ml of ethanol were added was dried over anhydrous magnesium sulfate and filtered to remove insoluble materials. The filtrate was concentrated and purified by a column chromatography [developing solvent: dichloromethane-methanol (4:1)] to afford 7.66 g of 5-(aminomethyl)-2- chloropyridine as a yellow solid.

$^1$H NMR(CDCl$_3$): 1.60(2H,s), 3.90(2H,s), 7.28(1H,d,J= 8.5 Hz), 7.67(1H,dd,J=8.5, 2.5 Hz), 8.33(1H,d,J=2.5 Hz)

By the same method, 5-(aminomethyl)-2-bromopyridine, 5-(aminomethyl)-2-chlorothiazole, 3-cyanobenzylamine, 5-(aminomethyl)thiazole, 5-(aminomethyl)-2-methylthiazole, 5-(aminomethyl)-2-phenylthiazole and 5-(aminomethyl)-2-(trifluoromethyl)thiazole were obtained.

Reference Example 3

A mixture of 15.05 g of 2-chloro-5-(chloromethyl) pyridine and 50 ml of acetonitrile was dropwise added to a mixture of 36 g of 40% methylamine aqueous solution and 200 ml of acetonitrile during an hour at room temperature and stirred for an hour and a half. The reaction mixture was concentrated. The resulting residue to which 100 ml of water was added, was neutralized by sodium hydrogen carbonate, saturated with sodium chloride and extracted with dichloromethane (200 ml×2). The organic layer was dried over anhydrous magnesium sulfate, concentrated and purified by a column chromatography [developing solvent: dichloromethane-methanol (4:1)] to afford 8.77 g of 2-chloro-5-(methylaminomethyl)pyridine as a yellowish brown liquid.

$^1$H NMR(CDCl$_3$): 1.30(1H,br.s), 2.44(3H,s), 3.75(2H,s), 7.30(1H,d,J=8.4 Hz), 7.68(1H,dd,J=8.4, 2.4 Hz), 8.35(1H, d,J=2.4 Hz)

Reference Example 4

To a solution of 3.15 g of S,S'-dimethyl dithioiminocarbonate.hydrochloride and 30 ml of pyridine was dropwise added 6.30 g of triluoroacetic anhydride during 30 minutes in a water bath of 20° C., followed by stirring for 5 hours. The reaction mixture was concentrated. The residue to which 20 ml of water were added was extracted with dichloromethane (30 ml). The organic layer was dried over anhydrous magnesium sulfate and concentrated. The residue was purified by a column chromatography (developing solvent: dichloromethane) to afford 2.33 g of S,S'-dimethyl N-trifluoroacetyldithioiminocarbonate as a yellow liquid.

$^1$H NMR(CDCl$_3$): 2.66(s)

Reference Example 5

A solution of 0.89 g of 5-aminomethyl-2-chloropyridine in 5 ml of isopropyl alcohol was dropwise added to a mixture of 1.0 g of S,S'-dimethyl N-cyanodithioiminocarbonate in 15 ml of isopropyl alcohol during 30 minutes, under refluxing. The mixture was further refluxed for an hour and a half and then ice-cooled. The resulting white solid was collected by filtration, by which 1.35 g of 1-(6-chloro-3-pyridylmethyl)-3-cyano-2-methylisourea were obtained.

$^1$H NMR(CDCl$_3$): 2.63(3H,s), 4.51(2H,d,J=6 Hz), 7.51 (1H,d,J=8 Hz), 7.83(1H,dd,J=8.3Hz), 8.38(1H,d,J=3 Hz), 8.95(1H,br.s)

By the same method, 1-(6-chloro-3-pyridylmethyl)-2-methyl-3-trifluoroacetylisothiourea, 1-(6-chloro-3-pyridylmethyl)-1,2-dimethyl-3-trifluoroacetylisothiourea and 1-(2-chloro-5-thiazolylmethyl)-3-cyano-2-methylisothiourea were obtained.

Reference Example 6

60% sodium hydride (in mineral oil) (0.80 g) was washed with petroleum ether and suspended in 20 ml of dimethylformamide (DMF). To the suspension was dropwise added a solution of 2.58 g of 3-cyano-1,2-dimethylisothiourea in 10 ml of DMF during 10 minutes at room temperature. After stirring for an hour, 3.24 g of 2-chloro-5-(5-chloromethyl) pyridine were added to the reacting mixture in 5 minutes, followed by stirring for 15 hours at room temperature. DMF was distilled off under reduced pressure, and the residue to which 100 ml of dichloromethane were added was washed with water. The organic layer was dried over anhydrous magnesium sulfate, concentrated and purified by a column chromatography [developing solvent: chloroform-ethanol (20:1)] to afford 3.50 g of 1-(6-chloro-3-pyridyl-methyl)-3-cyano-1,2-dimethylisothiourea as a yellow liquid.

$^1$H NMR(CDCl$_3$): 2.84(3H,s), 3.20(3H,s), 4.82(2H,s), 7.35(1H,d,J=8 Hz), 7.63(1H,dd,J=8.2 Hz), 8.31(1H,d,J=2 Hz)

By the same method, 1-(6-chloro-3-pyridylmethyl)-3-cyano-1-ethyl-2-methylisothiourea, 1-(6-chloro-3-pyridylmethyl)-1,2-dimethyl-3-nitroisothiourea, 1-(6-chloro-3-pyridylmethyl)-1-ethyl-2-methyl-3-nitroisothiourea, 1-(2-chloro-5-thiazolylmethyl)-1-ethyl-2-methyl-3-nitroisothiourea and 1-(2-chloro-5-thiazolylmethyl)-1,2-dimethyl-3-nitroisothiourea were obtained.

Reference Example 7

A mixture of 4.07 g of 2-chloro-5-aminopyridine, 2.55 g of methyl isothiocyanate and 30 ml of acetonitrile was refluxed for 13.5 hours, to which 0.70 g of additional methyl isothiocyanate was added and the mixture was refluxed for 3.5 hours. The reaction mixture was concentrated, and the residue was purified by a column chromatography [developing solvent: dichloromethaneethyl acetate (1:1)] to afford 4.51 g of 1-(6-chloro-3-pyridyl)-3-methylthiourea.

mp 164°–164.5° C. (recrystallized from acetonitrile) $^1$H NMR(CDCl$_3$): 3.12(3H,d,J=4.8 Hz), 6.86(1H,br.q,J=4.8 Hz), 7.33(1H,d,J=8.5 Hz), 7.86(1H,dd,J=8.5, 2.8 Hz), 8.31 (1H,d,J=2.8 Hz), 8.63(1H,br.s)

Reference Example 8

A mixture of 4.45 g of 2-bromo-5-methylthiazole, 4.89 g of N-bromosuccinimide, 0.2 g of benzoyl peroxide and 50 ml of carbon tetrachloride was refluxed for 50 minutes and then cooled to room temperature. An insoluble substance was removed by filtration and the filtrate was concentrated. The residue was purified by a column chromatography [developing solvent: hexane-dichloromethane (2:3)] to afford 4.53 g of 2-bromo-5-(bromomethyl)thiazole as a yellow solid.

$^1$HNMR(CDCl$_3$): 4.64(2H,s), 7.54(1H,s)

By the same method, 5-(bromomethyl)-3-(difluoromethyl)-2-thiazolone was obtained.

Reference Example 9

To a mixture of 1.85 g of potassium phthalimide and 20 ml of dry DMF were added 2.57 g of 2-bromo-5-(bromomethyl)thiazole by portions at room temperautre, taking for 20 minutes, followed by stirring for an hour. An insoluble substance was removed by filtration and the filtrate was concentrated. To the residue were added 30 ml of ethanol to which 0.60 g of hydrazine hydrate were dropwise added within 2 minutes in an oil bath of 20° C. The reaction mixture was refluxed for an hour and concentrated. After adding 20 ml of water and 10 ml of conc. hydrobromic acid, the mixture was further refluxed for 30 minutes. After cooling, the mixture was neutralized with 20% aqueous sodium hydroxide solution and concentrated. To the residue were 50 ml of acetonitrile, and an insoluble substance was removed by filtration. The filtrate was concentrated and the residue was purified by a column chromatography [developing solvent: dichloromethane-methanol (5:1)] to afford 0.76 g of 5-(aminomethyl)-2-bromothiazole as a brown oil.

$^1$HNMR(CDCl$_3$): 1.59(2H,s), 4.06(2H,d,J=1.2 Hz), 7.40 (1H,t,J=1.2 Hz)

Reference Example 10

To a mixture of 1.35 g of S-methyl-N-nitroisothiourea and 5 ml of acetonitrile was added 0.88 g of diethylamine, followed by stirring for 6 hours in an oil bath of 60° C. The reaction mixture was concentrated and the residue was purified by a column chromatography [developing solvent: dichloromethanemethanol (20:1)] to afford 0.85 g of N,N-diethyl-N'-nitroguanidine as a white solid.

mp 96°–97° C.

$^1$HNMR(CDCl$_3$): 1.23(6H,t,J=7.2 Hz), 3.47(4H,q,J=7.2 Hz), 7.93(2H,br.s)

Reference Example 11

To a mixture of 1.0 g of S-methyl-N-nitroisothiourea and 15 ml of acetonitrile was dropwise added 0.61 g of pyrrolidine within 2 minutes, followed by stirring for 30 minutes. The reaction mixture was concentrated. The resulting precipitate was washed with ethyl ether to afford 1.09 g of 1-(N-nitroamidino)pyrrolidine as white crystals.

mp 188°–191° C. $^1$HNMR(DMSO-d$_6$): 1.7–2.1(4H,m), 3.2–3.5(4H,m), 8.19(2H,br.s)

By the same method, N-ethyl-N-methyl-N'-nitroguanidine, mp 124°–125° C., was obtained.

Reference Example 12

To a mixture of 5.0 g of S-methyl-N-nitroisothiourea and 25 ml of pyridine was dropwise added 11.3 g of acetic anhydride at room temperature, taking for 10 minutes, followed by stirring for 5 hours at the same temperature. The reaction mixture was concentrated, and the residue was poured into 50 ml of 2N-hydrochloric acid. The resulting solid was collected by filtration and dried to obtain 5.1 g of N-acetyl-S-methyl-N'-nitroisothiourea. mp. 109°–110° C.

$^1$HNMR(CDCl$_3$): 2.30(3H,s), 2.42(3H,s), 11.20–12.00 (1H,br.)

Reference Example 13

To a mixture of 11.5 g of 2-hydroxy-5-methylthiazole (5-methyl-2-thiazolone), 100 ml of dioxane and 100 g of 40% sodium hydroxide aqueous solution was bubbled chlorodifluoromethane (gas) in an oil bath of 80° C. for an hour. The reaction mixture was poured into 500 ml of water and extracted twice with ethyl ether. The combined ethyl ether layer was dried over anhydrous magnesium sulfate and concentrated. The residue was subjected to a column chromatography [developing solvent: dichloromethane-hexane (1:1)], to separate 2.0 g of 2-(difluoromethoxy)-5-methylthiazole [$^1$HNMR (CDCl$_3$): 2.35(3H,d,J=1.5 Hz), 6.88(1H,br.q,J=1.5 Hz), 7.18(1H,t,J=72.0 Hz)] and 4.0 g of 3-(difluoromethyl)-5-methyl-2-thiazolne [$^1$HNMR(CDCl$_3$): 2.16(3H,d,J=1.5 Hz), 6.51(1H,br.q,J=1.5 Hz), 7.07(1H,t,J=60.0 Hz)], both being pale yellowish liquid.

Reference Example 14

A mixture of 11.22 g of 2,2,2,-trifluorothioacetamide and 10.14 g of ethyl 2-chloro-2-formylacetate was stirred for 30 minutes in an oil bath of 70° C. and then for 1.5 hours in an oil bath of 100° C., to which 100 ml of dichloromethane were added. After removing an insoluble substance, the mixture was concentrated and the residue was subjected to a column chromatography [developing solvent: hexane-ethyl acetate (10:1)], to obtain 3.74 g of ethyl 2-(trifluoromethyl)-5-thiazolecarboxylate as yellow liquid.

$^1$HNMR(CDCl$_3$): 1.41(3H,t,J=7.2 Hz), 4.43(2H,q,J=7.2 Hz), 8.50(1H,s)

A solution of 2.51 g of the above product in 10 ml of dry THF was dropwise added to a mixture of 0.50 g of lithium aluminum hydride in 80 ml of dry THF at room temperature, taking for 45 minutes, followed by stirring for 30 minutes. To the reaction mixture which was cooled by a freezing mixture were dropwise added in turn 0.5 ml of water, 0.5 ml of 10% sodium hydroxide aqueous solution and 1.5 ml of water. Then the mixture was stirred for 10 minutes in an ice bath and for 30 minutes at room temperature, and filtered through celite to remove an insoluble substance. The filtrate was concentrated. The residue to which 100 ml of chloroform were added was dried over anhydrous magnesium sulfate and concentrated to obtain 1.24 g of 5-(hydroxymethyl)-2-(trifluoromethyl)thiazole as brown liquid.

$^1$HNMR(CDCl$_3$): 3.45(1H,br.s), 4.93(2H,s), 7.77(1H,s)

A solution of 0.80 g of the above produce in 2 ml of 1,2-dichloroethane was dropwise added to a mixture of 0.4 ml of thionyl chloride and 1 ml of 1,2-dichloroethnae at 40° C., taking for 10 minutes, followed by stirring for an hour at the same temperature. Dichloromethane (2 ml) and water (2 ml) were added to the reaction mixture, which was adjusted to pH 7 (in the aqueous layer) by addition of sodium bicarbonate under stirring. The organic layer was separated and the aqueous layer was extracted with dichloromethane. The combined organic layers were filtered to remove an insoluble substance. The resulting layer was washed with a saturated saline solution, dried over anhydrous magnesium sulfate and concentrated to obtain 0.74 g of 5-(chloromethyl)-2-(trifluoromethyl)thiazole as red brown liquid.

$^1$HNMR(CDCl$_3$): 4.84(2H,s), 7.90(1H,s)

Example 1

To a mixture of 0.42 g of 1-(6-chloro-3-pyridylmethyl)-3-cyano-1-ethyl-2-methylisothiourea and 5 ml of acetonitrile was added each 0.5 g of 40% methylamine aqueous solution at an hour interval in total six time (3.0 g), while refluxing and stirring. The reaction mixture was stirred for 6 hours in total. Then, the mixture was concentrated to afford 0.32 g of 1-(6-chloro-3-pyridylmethyl)-2-cyano-1-ethyl-3-methylguanidine (Compound No. 3).

mp 122°–123° C. $^1$H NMR(DMSO-d$_6$): 1.07(3H,t,J=7 Hz), 3.00(3H,d,J=5 Hz), 3.35(2H,q,J=7 Hz), 4.62(2H,s), 7.23(1H,br.s), 7.50(1H,d,J=8 Hz), 7.78(1H,dd,J=8, 3 Hz), 8.33(1H,d,J=3 Hz)

Example 2

To a suspension of 0.44 g of 60% sodium hydride (in mineral oil) in 10 ml of DMF was added 1.32 g of N,N-dimethyl-N'-nitroguanidine during 20 minutes at room temperature. After stirring for 10 minutes, 1.62 g of 2-chloro-5-(chloromethyl)pyridine was added to the mixture in 5 minutes, and stirred for 2 hours at room temperature and for 4 hours in an oil bath of 60° C. After filtering insoluble materials off, the filtrate was concentrated. The resulting residue was purified by a column chromatography [developing solvent: dichloromethane-ethyl acetate (5:1–3:1)] to obtain 0.82 g of 1-(6-chloro-3-pyridylmethyl)-3,3-dimethyl-2-nitroguanidine (Compound No. 6).

mp 160.5°–162.5° C. Elemental analysis (C$_9$H$_{12}$N$_5$O$_2$Cl) calculated: C; 41.95, H; 4.69, N; 27.18 found : C; 41.73, H; 4.59, N; 26.94 $^1$H NMR(CDCl$_3$): 3.10(6H,s), 4.49(2H,br.s), 7.27(1H,d,J=8.5 Hz), 7.70(1H,dd,J=8.5, 2.5 Hz), 8.2–8.5 (2H,m)

Example 3

A mixture of 0.45 g of 1,2-dimethyl-3-nitroisothiourea, 0.43 g of 5-(aminomethyl)-2-chloropyridine and 25 ml of ethanol was refluxed for 6 hours and concentrated. The residue was purified by a column chromatography [developing solvent: chloroform-ethanol (5:1)] to afford 0.25 g of 1-(6-chloro-3-pyridylmethyl)-3-methyl-2-nitroguanidine (Compound No. 5).

mp 150°–152° C. Elemental analysis (C$_8$H$_{10}$N$_5$O$_2$Cl) calculated: C; 39.44, H; 4.14, N; 28.74 found : C; 39.92, H; 4.12, N; 28.91 $^1$H NMR(CDCl$_3$-DMSO-d$_6$): 2.94(3H,d,J=5 Hz), 4.51(2H,d,J=5 Hz), 7.32(1H,d,j=8 Hz), 7.75(1H,dd,J=8, 2 Hz), 7.82(1H,br.s), 8.37(1H,d,J=2 Hz), 8.90(1H,br.s)

Example 4

A mixture of 0.676 g of S-methyl-N-nitroisothiourea, 0.783 g of 2-chloro-5-(methylaminomethyl)pyridine and 6 ml of acetonitrile was refluxed for 17 hours, and concentrated. The residue was recrystallized from ethanol to obtain 0.38 g of 1-(6-chloro-3-pyridylmethyl)-1-methyl-2-nitroguanidine (Compound No. 7).

mp 167°–170° C. Elemental analysis (C$_8$H$_{10}$N$_5$O$_2$Cl) calculated: C; 39.44, H; 4.14, N; 28.74 found : C; 39.89, H; 4.07, N; 28.85 $^1$H NMR(DMSO-d$_6$): 3.01(3H,s), 4.70(2H,s), 7.48(1H,d,J=8.4 Hz), 7.78(1H,dd,J=8.4, 2.2 Hz), 8.37(1H, d,J=2.2 Hz), 8.56(2H,br.s)

Example 5

A mixture of 0.82 g of 1-(6-chloro-3-pyridyl-methyl)-1,2-dimethyl-3-nitroisothiourea, 0.464 g of 40% methylamine aqueous solution and 10 ml of acetonitrile was stirred for 2 hours at 70° C., and concentrated. The residue was purified by a column chromatography developing solution: dichloromethane-methanol [10:1]) to afford 0.56 g of 1-(6-chloro-3-pyridylmethyl)-1,3-dimethyl-2-nitroguanidine (Compound No. 8).

mp 136°–137° C.

Elemental analysis (C$_9$H$_{12}$N$_5$O$_2$Cl) calculated: C; 41.95, H; 4.69, N; 27.18 found : C; 41.89, H; 4.75, N; 27.15 $^1$H NMR(CDCl$_3$): 2.96(3H,d,J=4.8 Hz), 3.05(3H,s), 4.67(2H, s), 7.33(1H,d,J=8.3 Hz), 7.68(1H,dd,J=8.3, 2.4 Hz), 7.96 (1H,br.q,J=4.8 Hz), 8.30(1H,d,J=2.4 Hz)

Example 6

A mixture of 0.53 g of nitroguanidine, 0.61 g of 3-(aminomethyl)pyridine and 10 ml of water was stirred for 1.5 hours at 70°–80° C. and allowed to stand over night at room temperature. The precipitate collected by filtration was washed with ethanol to obtain 0.48 g of N-nitro-N'-(3-pyridylmethyl)guanidine (Compound No. 12).

mp 185°–190° C. $^1$H NMR(DMSO-d$_6$): 4.47(2H,d,J=5 Hz), 7.40(1H,dd,J=6, 4 Hz), 7.67–7.85(1H,m), 7.85–8.30 (2H,br.s), 8.47–8.67(2H,m)

Example 7

To a mixture of 0.24 g of 1-(6-chloro-3-pyridylmethyl)-3,3-dimethyl-2-nitroguanidine (Compound No. 6) and 6 ml of dry tetrahydrofuran (THF) was added 0.045 g of 60% sodium hydride (in mineral oil) at room temperature, followed by stirring for 30 minutes. A solution of 0.16 g of iodomethane in 1 ml of THF was added to the reaction mixture and allowed to react for 3 days. After adding 0.1 ml of acetic acid, the mixture was filtered to remove insoluble materials and the filtrate was concentrated. The residue was purified by a column chromatography [developing solvent: dichloromethanemethanol (20:1)] to obtain 0.17 g of 1-(6-chloro-3-pyridylmethyl)-1,3,3-trimethyl-2-nitroguanidine (Compound No. 14) as a white solid.

mp 99°–101° C. $^1$H MNR (CDCl$_3$): 2.90(3H,s), 3.02(6H, s), 4.03(2H,s), 7.38(1H,d,J=8.5 Hz), 7.79(1H,dd,J=8.5, 2.7 Hz), 8.37(1H,d,J=2.7 Hz)

Example 8

To a mixture of 0.26 g of 1-(6-chloro-3-pyridylmethyl)-3,3-dimethyl-2-nitroguanidine (Compound No. 6) and 3 ml of dry THF was added 0.08 g of 60% sodium hydride (in mineral oil) in a water bath of 20° C., followed by stirring for 30 minutes. A solution of 0.26 g of acetic formic anhydride in 0.5 ml of THF was added to the reaction mixture in one minute, and then stirred for 12 hours after the bath was removed. After adding 0.5 ml of acetic acid, the reaction mixture was concentrated. The residue was purified by a column chromatography [developing solvent: dichloromethanemethanol (30:1)] to obtain 0.10 g of 1-(6-chloro-3-pyridylmethyl)-1-formyl-3,3-dimethyl-2-nitroguanidine (Compound No. 22) as a syrup.

$^1$H NMR(CDCl$_3$): 3.03(6H,s), 4.70(2H,s), 7.36(1H,d,J= 8.7 Hz), 7.74(1H,dd,J=8.7, 2.7 Hz), 8.40(1H,d,J=2.7 Hz), 8.44(1H,s)

Example 9

A mixture of 0.20 g of 1-(6-chloro-3-pyridylmethyl) 3,3-dimethyl-2-nitroguanidine (Compound No. 6), 0.095 g of acetic anhydride and 1 ml of dry pyridine was stirred for 2 hours at 60° C. and for 5 hours at 100° C., and then concentrated. The residue was purified by a column chromatography [developing solvent: dichloromethanemethanol (40:1)] to obtain 0.12 g of 1-acetyl-1-(6-chloro-3-pyridylmethyl)-3,3-dimethyl-2-nitroguanidine (Compound No. 23) as a syrup (mixture of cis- and trans-isomers).

$^1$H NMR(CDCl$_3$): 2.10+2.16(3H,S+S), 2.6–3.3(6H,m), 4.1–5.2(2H,m), 7.23–7.45(1H,m), 7.67–7.90(1H,m), 8.30–8.50(1H,m)

Example 10

A mixture of 1.03 g of 1-(6-chloro-3-pyridyl)-3-methylthiourea, 0.32 g of cyanamide, 1.58 g of dicyclohexylcarbodiimide, 3 drops of ethyl diisopropylamine and 10 ml of acetonitrile was stirred for 34 hours at room temperature and filtered to collect an insoluble substance. The insoluble substance was recrystallized from a mixed solvent of acetonitrile and methanol, and then from acetonitrile to obtain 0.31 g of 1-(6-chloro-3-pyridyl)-2-cyano-3-methylguanidine (Compound No. 24).

mp 227°–228° C. Elemental analysis (C$_8$H$_8$N$_5$Cl) calculated: C; 45.84, H; 3.85, N; 33.41 found : C; 46.12, H; 3.68, N; 33.37 $^1$H NMR(DMSO-d$_6$): 2.85(3H,d,4.8 Hz), 7.2–7.65 (2H,m), 7.83(1H,dd,J=8.5, 3.0 Hz), 8.36(1H,d,J=3.0 Hz), 9.06(1H,br.s)

Example 11

A mixture of 0.39 g of 5-(aminomethyl)-2-bromothiazole, 0.30 g of 1,2-dimethyl-3-nitroisothiourea, 0.58 g of cuprous bromide, 0.55 g of anhydrous potassium carbonate and 4 ml of dry acetonitrile was stirred in an oil bath of 60° C. for 45 minutes. The reaction mixture was purified by a column chromatography [developing solvent: dichloromethanemethanol (10:1)] to obtain 1-(2-bromo-5-thiazolylmethyl)-3-methyl-2-nitroguanidine (Compound No. 39), as white solid.

mp 170° C. $^1$HNMR(DMSO-d$_6$): 2.81(3H,d,J=5.0 Hz), 4.51(2H,s), 7.60(1H,s), 8.08(1H,br.s), 8.93(1H,br,s)

Example 12

To a mixture of 0.5 g of N-acetyl-S-methyl-N'-nitroisothiourea and 5 ml of acetonitrile was dropwise added a solution of 0.44 g of 5-(aminomethyl)-2-chloropyridine in 3 ml of acetonitrile under ice-cooling, followed by stirring for 30 minutes under ice-cooling. The reaction mixture was concentrated and the residue was recrystallized from ethanol to afford 0.59 g of N-acetyl-N'-(6-chloro-3-pyridylmethyl)-N"-nitroguanidine (Compound No. 42) as white crystals.

mp 125°–126° C. $^1$HNMR(CDCl$_3$): 2.33(3H,s), 4.60(2H, d,J=6.0 Hz), 7.33(1H,d,J=7.8 Hz), 7.50–7.87(1H,m), 8.37 (1H,d,J=2.5 Hz), 9.70(1H,br.s), 11.85(1H,br.s)

The compound shown in Table 3 were prepared in accordance with the above-mentioned Examples 1–12 and the production method of the present invention. Besides, the compounds of the above-mentioned Examples are included in Table 3.

TABLE 3

R$^1$—(CH$_2$)$_n$—N(R$^2$)(R$^3$)C=N—X

| Compound No. | R$^1$ | n | R$^2$ | R$^3$ | X | Mp (°C.) | Preparation method (corresponding Example No.) |
|---|---|---|---|---|---|---|---|
| 1 | 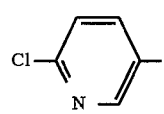 | 1 | H | MeNH | CN | 196–197 | 1 |
| 2 | 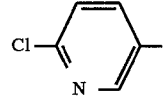 | 1 | Me | MeNH | CN | 121–122 | 1 |

TABLE 3-continued $$R^1-(CH_2)_n-\underset{R^3}{\underset{|}{N}}\overset{R^2}{\underset{}{|}}C=N-X$$

| Compound No. | R¹ | n | R² | R³ | X | Mp (°C.) | Preparation method (corresponding Example No.) |
|---|---|---|---|---|---|---|---|
| 3 | 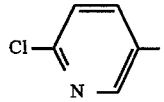 6-Cl-pyridin-3-yl | 1 | Et | MeNH | CN | 122–123 | 1 |
| 4 | 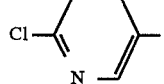 6-Cl-pyridin-3-yl | 1 | Me | 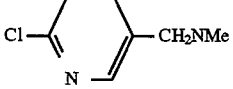 6-Cl-pyridin-3-yl-CH₂NMe | CN | (Syrup)ª⁾ | 2 |
| 5 | 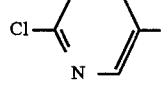 6-Cl-pyridin-3-yl | 1 | H | MeNH | NO₂ | 150–152 | 3 |
| 6 | 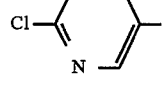 6-Cl-pyridin-3-yl | 1 | H | Me₂N | NO₂ | 160.5–162.6 | 2 |
| 7 | 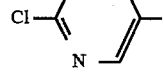 6-Cl-pyridin-3-yl | 1 | Me | NH₂ | NO₂ | 167–170 | 4 |
| 8 | 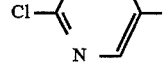 6-Cl-pyridin-3-yl | 1 | Me | MeNH | NO₂ | 136–137 | 5 |
| 9 | 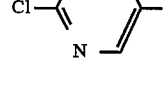 6-Cl-pyridin-3-yl | 1 | H | EtNH | NO₂ | 137.5–138 | 3 |
| 10 | 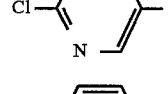 6-Cl-pyridin-3-yl | 1 | H | 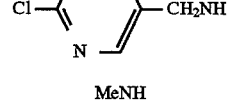 6-Cl-pyridin-3-yl-CH₂NH | NO₂ | 213–215.5 | 2 |
| 11 | 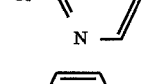 6-Cl-pyridin-3-yl | 1 | H | MeNH | COCF₃ | 121–122 | 5 |
| 12 | 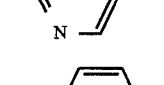 pyridin-3-yl | 1 | H | H₂N | NO₂ | 185–190 | 6 |
| 13 | 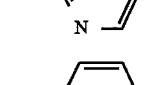 6-Cl-pyridin-3-yl | 1 | Et | MeNH | NO₂ | 114.5–115 | 5 |
| 14 | 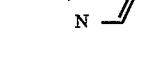 6-Cl-pyridin-3-yl | 1 | Me | Me₂N | NO₂ | 99–101 | 7 |

TABLE 3-continued $$R^1-(CH_2)_n-\underset{R^3}{\overset{R^2}{N}}\underset{}{\overset{}{\underset{}{C}}}=N-X$$

| Compound No. | R¹ | n | R² | R³ | X | Mp (°C.) | Preparation method (corresponding Example No.) |
|---|---|---|---|---|---|---|---|
| 15 | 2-Cl-pyridin-5-yl | 1 | H | H₂N | NO₂ | 195–197 | 6 |
| 16 | 2-Cl-pyridin-5-yl | 1 | Et | H₂N | NO₂ | 137–139 | 5 |
| 17 | pyridin-3-yl | 1 | H | MeNH | NO₂ | 169–171 | 3 |
| 18 | 2-Br-pyridin-5-yl | 1 | H | MeNH | NO₂ | (amorphous)[b] | 3 |
| 19 | 2-Cl-thiazol-5-yl | 1 | H | MeNH | NO₂ | 172–173 | 3 |
| 20 | 4-Cl-phenyl | 1 | H | MeNH | NO₂ | 188–190.5 | 3 |
| 21 | 3-CN-phenyl | 1 | H | MeNH | NO₂ | 133–135 | 3 |
| 22 | 2-Cl-pyridin-5-yl | 1 | CHO | Me₂N | NO₂ | (syrup)[c] | 8 |
| 23 | 2-Cl-pyridin-5-yl | 1 | COMe | Me₂N | NO₂ | (syrup)[d] | 9 |
| 24 | 2-Cl-pyridin-5-yl | 0 | H | MeNH | CN | 227–228 | 10 |
| 25 | 2-Cl-thiazol-5-yl | 1 | H | Me₂N | NO₂ | 154–159 | 2 |
| 26 | 2-Cl-thiazol-5-yl | 1 | Et | MeNH | NO₂ | (syrup)[e] | 5 |

TABLE 3-continued $$R^1-(CH_2)_n-N\begin{matrix}R^2\\ \\R^3\end{matrix}C=N-X$$

| Compound No. | R¹ | n | R² | R³ | X | Mp (°C.) | Preparation method (corresponding Example No.) |
| --- | --- | --- | --- | --- | --- | --- | --- |
| 27 | 2-Cl-thiazol-5-yl | 1 | COMe | Me₂N | NO₂ | 127–129 | 9 |
| 28 | 6-Cl-pyridin-3-yl | 1 | Me | H₂N | COCF₃ | 181–184 | 5 |
| 29 | 2-Cl-thiazol-5-yl | 1 | Me | MeNH | NO₂ | (syrup)f) | 5 |
| 30 | 2-Cl-thiazol-5-yl | 1 | Me | H₂N | NO₂ | 121–122 | 5 |
| 31 | thiazol-5-yl | 1 | H | MeNH | NO₂ | 157–166 | 3, 11 |
| 32 | 2-Me-thiazol-5-yl | 1 | H | Me₂N | NO₂ | 173–174 | 2 |
| 33 | 2-Me-thiazol-5-yl | 1 | H | MeNH | NO₂ | 175–179 | 3, 11 |
| 34 | 2-Ph-thiazol-5-yl | 1 | H | MeNH | NO₂ | 171–173 | 3, 11 |
| 35 | 2-Cl-thiazol-5-yl | 1 | H | Me(Et)N | NO₂ | (syrup)g) | 2 |
| 36 | 2-Cl-thiazol-5-yl | 1 | H | Me(Et)N | NO₂ | 165–167 | 2 |
| 37 | 2-Cl-thiazol-5-yl | 1 | H | pyrrolidin-1-yl | NO₂ | 185–188 | 2 |
| 38 | 2-Cl-thiazol-5-yl | 1 | Me | Me₂N | NO₂ | 103–104 | 7 |
| 39 | 2-Br-thiazol-5-yl | 1 | H | MeNH | NO₂ | 170 | 11 |

TABLE 3-continued $$R^1-(CH_2)_n-N\underset{R^3}{\overset{R^2}{\diagdown}}C=N-X$$

| Compound No. | R¹ | n | R² | R³ | X | Mp (°C.) | Preparation method (corresponding Example No.) |
|---|---|---|---|---|---|---|---|
| 40 | Br-[thiazole] | 1 | H | Me₂N | NO₂ | 185–187 | 2 |
| 41 | Cl-[thiazole] | 1 | H | MeNH | CN | 171–173 | 1 |
| 42 | Cl-[pyridine] | 1 | H | MeCONH | NO₂ | 125–126 | 12 |
| 43 | Ph | 1 | H | MeCONH | NO₂ | 107–109 | 12 |
| 44 | Cl-[thiazole] | 1 | H | MeCONH | NO₂ | 132–133 | 12 |
| 45 | Cl-[pyridine] | 1 | Et | MeCONH | NO₂ | 175–176 | 12 |
| 46 | CHF₂-N-[oxazole] | 1 | H | Me₂N | NO₂ | (syrup)ʰ⁾ | 2 |
| 47 | CF₃-[thiazole] | 1 | H | MeNH | NO₂ | 119–121 | 11 |
| 48 | [pyridine] | 1 | H | MeNH | NO₂ | 178–180 | 3 | a)¹HNMR(CDCl₃): 2.87(6H, s), 4.59(4H, s), 7.37(2H, d, J=8Hz), 7.72(2H, dd, J=8, 2Hz), 8.37(2H, d, J=2Hz).
b)¹HNMR(CDCl₃): 3.00(3H, d, J=4Hz), 4.53(2H, d, J=6Hz), 6.76(1H, br.s), 7.46(1H, d, J=8Hz), 7.67(1H, dd, J=8, 3Hz), 8.20(1H, d, J=3Hz), 8.83(1H, br.s).
c)¹HNMR(CDCl₃): mentioned in Example 8
d)¹HNMR(CDCl₃): mentioned in Example 9
e)¹HNMR(CDCl₃): 1.26(3H, t, J=7Hz), 2.98(3H, d, J=2Hz), 3.47(2H, q, J=7Hz), 4.70(2H, s), 7.50(1H, s,), 7.96(1H, br.s).
f)¹HNMR(CDCl₃): 3.00(3H, d, J=4Hz), 3.09(3H, s), 4.69(2H, s), 7.50(1H, s), 8.00(1H, br.s).
g)¹HNMR(CDCl₃): 1.23(6H, t, J=7Hz), 3.46(4H, q, J=7.2Hz), 4.60(2H, br.s), 7.44(1H, s), 8.30(1H, br.s).
h)¹HNMR(CDCl₃): 3.11(6H, s), 4.42(2H, d, J=6.0Hz), 6.86(1H, s), 7.07(1H, t, J=60.0Hz), 7.78(1H, br.t, J=6.0Hz).

Example 13
An emulsifiable concentrate was prepared by well-mixing 20 wt % of Compound No. 1, 75 wt % of xylene and 5 wt % of polyoxyethylene glycol ether (Nonipol 85®).

Example 14
Wettable powders were prepared by well-mixing 30 wt % of Compound No. 6, 5 wt % of sodium ligninsulfonate, 5 wt % of polyoxyethylene glycol ether (Nonipol 85®), 30 wt % of white carbon and 30 wt % of clay.

Example 15
A dust was prepared by well mixing 3 wt % of Compound No. 7, 3 wt % of white carbon and 94 wt % of clay.

Example 16
Granules were prepared by thoroughly pulverizing and mixing 10 wt % of Compound No. 8, 5 wt % of sodium ligninsulfonate and 85 wt % of clay, kneading the mixture with water, granulating and drying the resultant.

What we claim is:
1. An insecticidal composition comprising a guanidine derivative of the formula (I):

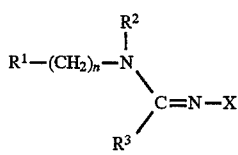

wherein $R^1$ is an optionally substituted homocyclic or heterocyclic ring selected from the group consisting of $C_{3-8}$ cycloalkyl, $C_{3-8}$ cycloalkenyl, $C_{6-14}$ aryl, 2- or 3-thienyl, 2- or 3-furyl, 2- or 3-pyrrolyl, 2-, 3- or 4-pyridyl, 2-, 4- or 5-oxazolyl, 2-, 4- or 5-thiazolyl, 3-, 4- or 5-pyrazolyl, 2-, 4- or 5-imidazolyl, 3-, 4- or 5-isoxazolyl, 3-, 4- or 5-isothiazolyl, 3- or 5-(1,2,4-oxadiazolyl), 1,3,4-oxadiazolyl, 3- or 5-(1,2,4-thiadiazolyl), 1,3,4-thiadiazolyl, 4- or 5-(1,2,3-thiadiazolyl), 1,2,5-thiadiazolyl, 1,2,3-triazolyl, 1,2,4-triazolyl, 1H- or 2H-tetrazolyl, N-oxido-2-, 3- or 4- pyridyl, 2-, 4- or 5-pyrimidinyl, N-oxido-2-, 4- or 5-pyrimidinyl, 3- or 4-pyridazinyl, pyrazinyl, N-oxido-3- or 4-pyridazinyl, benzofuryl, benzothiazolyl, benzoxazolyl, triazinyl, oxotriazinyl, tetrazolo(1,5-b)pyridazinyl, triazolo (4,5-b)pyridazinyl, oxoimidazinyl, dioxotriazinyl, pyrrolidinyl, piperidinyl, pyranyl, thiopyranyl, 1,4-oxazinyl, morpholinyl, 1,4-thiazinyl, 1,3-thiazinyl, piperazinyl, benzoimidazolyl, quinolyl, isoquinolyl, cinnolinyl, phthalazinyl, quinazolinyl, quinoxalinyl, indolizinyl, quinolizinyl, 1,8-naphthyridinyl, purinyl, pteridinyl, dibenzofuranyl, carbazolyl, acridinyl, phenanthridinyl, phenazinyl, phenothiazinyl and phenoxazinyl, the homocyclic and the heterocyclic rings optionally being substituted with up to 5 substituents selected from the group consisting of $C_{1-15}$ alkyl, $C_{3-10}$ cycloalkyl, $C_{2-10}$ alkenyl, $C_{2-10}$ alkynyl, $C_{3-10}$ cycloalkenyl, $C_{6-10}$ aryl, $C_{7-10}$ aralkyl, nitro, hydroxy, mercapto, oxo, thioxo, cyano, carbamoyl, carboxyl, $C_{1-4}$ alkoxycarbonyl, sulfo, halogen, $C_{1-4}$ alkoxy, $C_{6-10}$ aryloxy, $C_{1-4}$ alkylthio, $C_{6-10}$ arylthio, $C_{1-4}$ alkylsulfinyl, $C_{6-10}$ arylsulfinyl, $C_{1-4}$ alkylsulfonyl, $C_{6-10}$ arylsulfonyl, amino, $C_{2-6}$ acylamino, mono- or di-$C_{1-4}$ alkylamino, $C_{3-6}$ cycloalkylamino, $C_{6-10}$ arylamino, $C_{2-4}$ acyl, $C_{6-10}$ arylcarbonyl, and a 5- or 6-membered heterocyclic group having 1 to 4 heteroatoms selected from oxygen, sulfur and nitrogen, wherein when the substituent is the $C_{6-10}$ aryl, $C_{7-10}$ aralkyl, $C_{3-10}$ cycloalkyl, $C_{3-10}$ cycloalkenyl, $C_{6-10}$ aryloxy, $C_{6-10}$ arylthio, $C_{6-10}$ arylsulfinyl, $C_{6-10}$ arylsulfonyl, $C_{6-10}$ arylamino or heterocyclic group, the substituent may be further substituted by 1 to 5 of halogen, hydroxy, $C_{1-4}$ alkyl, $C_{2-4}$ alkenyl, $C_{2-4}$ alkynyl, $C_{6-10}$ aryl, $C_{1-4}$ alkoxy, phenoxy, $C_{1-4}$ alkylthio, or phenylthio, and when the substituent is $C_{1-15}$ alkyl, $C_{2-10}$ alkenyl, $C_{2-10}$ alkynyl, $C_{1-4}$ alkoxy, $C_{1-4}$ alkylthio, $C_{1-4}$ alkylsulfinyl, $C_{1-4}$ alkylsulfonyl, amino, mono- or di-$C_{1-4}$ alkylamino, $C_{3-6}$ cycloalkylamino or $C_{6-10}$ arylamino, the substituent may be further substituted by 1 to 5 of halogen, hydroxy, $C_{1-4}$ alkoxy or $C_{1-4}$ alkylthio, $R^2$ is hydrogen or an optionally substituted hydrocarbon selected from the group consisting of $C_{1-15}$ alkyl, $C_{3-10}$ cycloalkyl, $C_{2-10}$ alkenyl, $C_{2-10}$ alkynyl, $C_{3-10}$ cycloalkenyl, $C_{6-10}$ aryl or $C_{7-10}$ aralkyl, each of which may be unsubstituted or substituted by one to five of the groups mentioned as substituents of $R^1$, $R^3$ is an amino group represented by the formula:

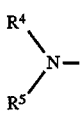

wherein $R^4$ and $R^5$ are, the same or different, a hydrogen atom or an optionally substituted hydrocarbon group or both $R^4$ and $R^5$ are combined with the adjacent nitrogen atom to form a cyclic amino group, the hydrocarbon group being selected from the group consisting of $C_{1-15}$ alkyl, $C_{3-10}$ cycloalkyl, $C_{2-10}$ alkenyl, $C_{2-10}$ alkynyl, $C_{3-10}$ cycloalkenyl, $C_{6-10}$ aryl and $C_{7-10}$ aralkyl, the substituent of the hydrocarbon group being selected from the group consisting of those mentioned in said substituents of $R^1$, and the cyclic amino group being selected from the group consisting of aziridino, azetidino, pyrrolidino, morpholino and thiomorpholino, n is 0 or 1, and X is nitro, cyano or trifluoroacetyl, provided that when n is 0, $R^1$ is an optionally substituted heterocyclic group, or provided that when X is nitro, $R^1$ is an optionally substituted homocyclic or heterocyclic group as defined above, n is 0 or 1, $R^2$ is a substituted $C_{1-4}$ alkyl or optionally substituted $C_{5-15}$ alkyl, $C_{3-10}$ cycloalkyl, $C_{2-10}$ alkenyl, $C_{2-10}$ alkynyl, $C_{3-10}$ cycloalkenyl, $C_{6-10}$ aryl or $C_{7-10}$ aralkyl group, the substituents of group $R^2$ being selected from the group consisting of those mentioned as substituents of $R^2$ above, and $R^3$ is as defined above, or provided that when X is nitro, $R^1$ is an optionally substituted homocyclic or heterocyclic group as defined above, n is 0 or 1, $R^2$ is a hydrogen atom or $C_{1-4}$ alkyl, $R^3$ is a group represented by the formula:

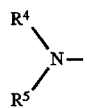

wherein one of $R^4$ and $R^5$ is a hydrogen atom or an optionally substituted hydrocarbon group selected from the group consisting of $C_{1-15}$ alkyl, $C_{3-10}$ cycloalkyl, $C_{2-10}$ alkenyl, $C_{2-10}$ alkynyl, $C_{3-10}$ cycloalkenyl, $C_{6-10}$ aryl and $C_{7-10}$ aralkyl, the substituent of the hydrocarbon group being selected from the group consisting of those mentioned as substituents of $R^1$, and the other is a substituted $C_{1-4}$ alkyl or an optionally substituted hydrocarbon group selected from the group consisting of $C_{5-15}$ alkyl, $C_{3-10}$ cycloalkyl, $C_{2-10}$ alkenyl, $C_{2-10}$ alkynyl, $C_{3-10}$ cycloalkenyl, $C_{6-10}$ aryl and $C_{7-10}$ aralkyl, the substituent of the $C_{1-4}$ alkyl and of the hydrocarbon group being selected from the group consisting of those mentioned as substituents of $R^1$, or both $R^4$ and $R^5$ are combined with the adjacent nitrogen atom to form a cyclic amino group selected from the group consisting of aziridino, azetidino, pyrrolidino, morpholino and thiomorpholino, or provided that when X is cyano, $R^1$ is 2-chloro-5-thiazolyl, n is 1, $R^2$ is hydrogen, and $R^3$ is methylamino, or a salt thereof, and a carrier or diluent.

2. The composition as claimed in claim 1, wherein when X is trifluoroacetyl, $R^1$ is an optionally substituted homocyclic or heterocyclic group as defined in claim 1, n is 0 or 1, $R^2$ is hydrogen or an optionally substituted hydrocarbon selected from the group consisting of $C_{1-15}$ alkyl, $C_{3-10}$ cycloalkyl, $C_{2-10}$ alkenyl, $C_{2-10}$ alkynyl, $C_{3-10}$ cycloalkenyl, $C_{6-10}$ aryl or $C_{7-10}$ aralkyl, each of which may be unsubstituted or substituted by one to five groups mentioned as substituents of $R^2$, and $R^3$ is as defined in claim 1.

3. The composition as claimed in claim 1, wherein X is nitro.

4. The composition as claimed in claim 1, wherein X is cyano.

5. A method of killing an insect comprising contacting an insect with an insecticidally effective amount of the composition of claim 1.

6. The composition as claimed in claim 1, wherein the heterocyclic group is a 5- or 6-membered heterocyclic group having at least one nitrogen atom.

7. The composition as claimed in claim 1, wherein $R^1$ is selected from the group consisting of pyridyl, halogenopyridyl and halogenothiazolyl.

8. The composition as claimed in claim 1, wherein $R^3$ is mono- or di-$C_{1-4}$ alkylamino or $C_{1-4}$ acylamino.

9. The composition as claimed in claim 1, wherein $R^3$ is mono- or di-methylamino.

10. The composition as claimed in claim 1, wherein $R^3$ is amino which is substituted with formyl or acetyl.

11. The composition as claimed in claim 1, wherein $R^4$ is formyl or acetyl, and $R^5$ is hydrogen or methyl.

12. The composition as claimed in claim 1, wherein $R^3$ is N-methyl-formamido.

13. A guanidine derivative of the formula ($I^a$):

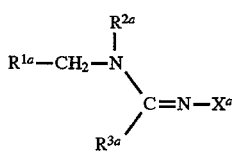
($I^a$)

wherein $R^{1a}$ is a heterocyclic ring selected from the group consisting of 2- or 3-thienyl, 2- or 3-furyl, 2- or 3-pyrrolyl, 2-, 3- or 4-pyridyl, 2-, 4- or 5-oxazolyl, 2-, 4- or 5-thiazolyl, 3-, 4- or 5-pyrazolyl, 2-, 4- or 5-imidazolyl, 3-, 4- or 5-isoxazolyl, 3-, 4- or 5-isothiazolyl, 3- or 5-(1,2,4-oxadiazolyl), 1,3,4-oxadiazolyl, 3- or 5-(1,2,4-thiadiazolyl), 1,3,4-thiadiazolyl, 4- or 5-(1,2,3-thiadiazolyl), 1,2,5-thiadiazolyl, 1,2,3-triazolyl, 1,2,4-triazolyl, 1H- or 2H-tetrazolyl, N-oxido-2-, 3- or 4- pyridyl, 2-, 4- or 5-pyrimidinyl, N-oxido-2-, 4- or 5-pyrimidinyl, 3- or 4-pyridazinyl, pyrazinyl, N-oxido-3- or 4-pyridazinyl, benzofuryl, benzothiazolyl, benzoxazolyl, triazinyl, oxotriazinyl, tetrazolo(1,5-b)pyridazinyl, triazolo(4,5-b)pyridazinyl, oxoimidazinyl, dioxotriazinyl, pyrrolidinyl, piperidinyl, pyranyl, thiopyranyl, 1,4-oxazinyl, morpholinyl, 1,4-thiazinyl, 1,3-thiazinyl, piperazinyl, benzoimidazolyl, quinolyl, isoquinolyl, cinnolinyl, phthalazinyl, quinazolinyl, quinoxalinyl, indolizinyl, quinolizinyl, 1,8-naphthyridinyl, purinyl, pteridinyl, dibenzofuranyl, carbazolyl, acridinyl, phenanthridinyl, phenazinyl, phenothiazinyl and phenoxazinyl, the heterocyclic ring optionally being substituted with up to 5 substituents selected from the group consisting of $C_{1-15}$ alkyl, $C_{3-10}$ cycloalkyl, $C_{2-10}$ alkenyl, $C_{2-10}$ alkynyl, $C_{3-10}$ cycloalkenyl, $C_{6-10}$ aryl, $C_{7-10}$ aralkyl, nitro, hydroxy, mercapto, oxo, thioxo, cyano, carbamoyl, carboxyl, $C_{1-4}$ alkoxycarbonyl, sulfo, halogen, $C_{1-4}$ alkoxy, $C_{6-10}$ aryloxy, $C_{1-4}$ alkylthio, $C_{6-10}$ arylthio, $C_{1-4}$ alkylsulfinyl, $C_{6-10}$ arylsulfinyl, $C_{1-4}$ alkylsulfonyl, $C_{6-10}$ arylsulfonyl, amino, $C_{2-6}$ acylamino, mono- or di-$C_{1-4}$ alkylamino, $C_{3-6}$ cycloalkylamino, $C_{6-10}$ arylamino, $C_{2-4}$ acyl, $C_{6-10}$ arylcarbonyl, and a 5- or 6-membered heterocyclic group having 1 to 4 heteroatoms selected from oxygen, sulfur and nitrogen, wherein when the substituent is the $C_{6-10}$ aryl, $C_{7-10}$ aralkyl, $C_{3-10}$ cycloalkyl, $C_{3-10}$ cycloalkenyl, $C_{6-10}$ aryloxy, $C_{6-10}$ arylthio, $C_{6-10}$ arylsulfinyl, $C_{6-10}$ arylsulfonyl, $C_{6-10}$ arylamino or heterocyclic group, the substituent may be further substituted by 1 to 5 of halogen, hydroxy, $C_{1-4}$ alkyl, $C_{2-4}$ alkenyl, $C_{2-4}$ alkynyl, $C_{6-10}$ aryl, $C_{1-4}$ alkoxy, phenoxy, $C_{1-4}$ alkylthio, or phenylthio, and when the substituent is $C_{1-15}$ alkyl, $C_{2-10}$ alkenyl, $C_{2-10}$ alkynyl, $C_{1-4}$ alkoxy, $C_{1-4}$ alkylthio, $C_{1-4}$ alkylsulfinyl, $C_{1-4}$ alkylsulfonyl, amino, mono- or di-$C_{1-4}$ alkylamino, $C_{3-6}$ cycloalkylamino or $C_{6-10}$ arylamino, the substituent may be further substituted by 1 to 5 of halogen, hydroxy, $C_{1-4}$ alkoxy or $C_{1-4}$ alkylthio, $R^{2a}$ is hydrogen or an optionally substituted hydrocarbon selected from the group consisting of $C_{1-15}$ alkyl, $C_{3-10}$ cycloalkyl, $C_{2-10}$ alkenyl, $C_{2-10}$ alkynyl, $C_{3-10}$ cycloalkenyl, $C_{6-10}$ aryl or $C_{7-10}$ aralkyl, each of which may be unsubstituted or substituted by one to five of the groups mentioned as substituents of $R^{1a}$, $R^{3a}$ is an amino group represented by the formula:

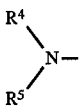

wherein $R^4$ and $R^5$ are, the same or different, a hydrogen atom or an optionally substituted hydrocarbon group or both $R^4$ and $R^5$ are combined with the adjacent nitrogen atom to form a cyclic amino group, the hydrocarbon group being selected from the group consisting of $C_{1-15}$ alkyl, $C_{3-10}$ cycloalkyl, $C_{2-10}$ alkenyl, $C_{2-10}$ alkynyl, $C_{3-10}$ cycloalkenyl, $C_{6-10}$ aryl and $C_{7-10}$ aralkyl, the substituent of the hydrocarbon group being selected from the group consisting of those mentioned in said substituents of the heterocyclic group designated by $R^{1a}$, and the cyclic amino group being selected from the group consisting of aziridino, azetidino, pyrrolidino, morpholino and thiomorpholino and $X^a$ is nitro or trifluoroacetyl, provided that when $X^a$ is nitro, $R^{1a}$ is an optionally substituted heterocyclic group as defined above, $R^{2a}$ is a substituted $C_{1-4}$ alkyl or optionally substituted $C_{5-15}$ alkyl, $C_{3-10}$ cycloalkyl, $C_{2-10}$ alkenyl, $C_{2-10}$ alkynyl, $C_{3-10}$ cycloalkenyl, $C_{6-10}$ aryl or $C_{7-10}$ aralkyl group, the substituents of group $R^{2a}$ being selected from the group consisting of those mentioned as substituents of $R^{2a}$ above, and $R^{3a}$ is as defined above, or provided that when $X^a$ is nitro, $R^{1a}$ is an optionally substituted heterocyclic group as defined above, $R^{2a}$ is a hydrogen atom or $C_{1-4}$ alkyl, $R^{3a}$ is a group represented by the formula:

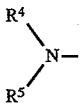

wherein one of $R^4$ and $R^5$ is a hydrogen atom or an optionally substituted hydrocarbon group selected from the group consisting of $C_{1-15}$ alkyl, $C_{3-10}$ cycloalkyl, $C_{2-10}$ alkenyl, $C_{2-10}$ alkynyl, $C_{3-10}$ cycloalkenyl, $C_{6-10}$ aryl and $C_{7-10}$ aralkyl, the substituent of the hydrocarbon group being selected from the group consisting of those mentioned as substituents of $R^{1a}$, and the other is a substituted $C_{1-4}$ alkyl or an optionally substituted hydrocarbon group selected from the group consisting of $C_{5-15}$ alkyl, $C_{3-10}$ cycloalkyl, $C_{2-10}$ alkenyl, $C_{2-10}$ alkynyl, $C_{3-10}$ cycloalkenyl, $C_{6-10}$ aryl and $C_{7-10}$ aralkyl, the substituent of the $C_{1-4}$ alkyl and of the hydrocarbon group being selected from the group consisting of those mentioned as substituents of $R^{1a}$, or both $R^4$ and $R^5$ are combined with the adjacent nitrogen atom to form a cyclic amino group selected from the group consisting of aziridino, azetidino, pyrrolidino, morpholino and thiomorpholino, or a salt thereof.

14. The guanidine derivative of claim 13, wherein when $X^a$ is trifluoroacetyl, $R^{1a}$ is an optionally substituted heterocyclic group as defined in claim 12, $R^{2a}$ is hydrogen or an optionally substituted hydrocarbon selected from the group consisting of $C_{1-15}$ alkyl, $C_{3-10}$ cycloalkyl, $C_{2-10}$ alkenyl, $C_{2-10}$ alkynyl, $C_{3-10}$ cycloalkenyl, $C_{6-10}$ aryl or $C_{7-10}$ aralkyl, each of which may be unsubstituted or substituted by one to five groups mentioned as substituents of $R^{2a}$, and $R^{3a}$ is as defined in claim 13.

15. The guanidine derivative as claimed in claim 13, wherein X is nitro.

16. The guanidine derivative as claimed in claim 13, wherein the heterocyclic group is a 5- or 6-membered heterocyclic group having at least one nitrogen atom.

17. The guanidine derivative as claimed in claim 13, wherein $R^{1a}$ is selected from the group consisting of pyridyl, halogenopyridyl and halogenothiazolyl.

18. The guanidine derivative as claimed in claim 13, wherein $R^{3a}$ is mono- or di-$C_{1-4}$ alkylamino or $C_{1-4}$ acylamino.

19. The guanidine derivative as claimed in claim 13, wherein $R^{3a}$ is mono- or di-methylamino.

20. The guanidine derivative as claimed in claim 13, wherein $R^{3a}$ is amino which is substituted with formyl or acetyl.

21. The guanidine derivative as claimed in claim 13, wherein $R^4$ is formyl or acetyl, and $R^5$ is hydrogen or methyl.

22. The guanidine derivative as claimed in claim 13, wherein $R^{3a}$ is N-methyl-formamido.

* * * * *